(12) United States Patent
Erekovcanski et al.

(10) Patent No.: US 11,344,715 B2
(45) Date of Patent: May 31, 2022

(54) FLUSH SYRINGE WITH DISINFECTING FEATURE

(71) Applicant: Becton, Dickinson and Company, Franklin Lakes, NJ (US)

(72) Inventors: Nicholas Erekovcanski, Butler, NJ (US); Roza Mahmoodian, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/254,747

(22) Filed: Jan. 23, 2019

(65) Prior Publication Data

US 2019/0232039 A1 Aug. 1, 2019

Related U.S. Application Data

(60) Provisional application No. 62/622,640, filed on Jan. 26, 2018.

(51) Int. Cl.
*A61M 39/16* (2006.01)
*A61M 5/34* (2006.01)
(Continued)

(52) U.S. Cl.
CPC ............ *A61M 39/162* (2013.01); *A61M 5/31* (2013.01); *A61M 5/3134* (2013.01);
(Continued)

(58) Field of Classification Search
CPC ...... A61M 39/16; A61M 39/162; A61M 5/31; A61M 5/3134; A61M 2005/3103;
(Continued)

(56) References Cited

U.S. PATENT DOCUMENTS 3,403,679 A 10/1968 Sinclair et al.
4,417,890 A * 11/1983 Dennehey ............. A61M 39/20
138/89
(Continued)

FOREIGN PATENT DOCUMENTS

CN 101631585 A 1/2010
CN 101980746 A 2/2011
(Continued)

OTHER PUBLICATIONS

PCT International Search Report and Written Opinion in PCT/US2019/015096 dated Mar. 21, 2019, 12 pages.
(Continued)

*Primary Examiner* — Brandy S Lee
*Assistant Examiner* — Hong-Van N Trinh
(74) *Attorney, Agent, or Firm* — Servilla Whitney LLC

(57) ABSTRACT

Flush syringe assemblies are described herein. Such flush syringe assembly may include a barrel including a side wall defining a chamber, an open proximal end, a distal end having a distal wall with an elongate tip extending distally therefrom having a passageway therethrough in fluid communication with said chamber. A collar may be mounted on the distal wall of the barrel and surrounding the elongate tip. A disinfectant-loaded swab may be disposed in the collar. The flush syringe assembly may also include a removable cap.

14 Claims, 45 Drawing Sheets

(51) Int. Cl.
*A61M 5/31* (2006.01)
*A61M 5/315* (2006.01)

(52) U.S. Cl.
CPC ...... *A61M 5/3146* (2013.01); *A61M 5/31505* (2013.01); *A61M 5/34* (2013.01); *A61M 39/16* (2013.01); *A61M 2005/3117* (2013.01); *A61M 2005/31508* (2013.01); *A61M 2205/0205* (2013.01)

(58) Field of Classification Search
CPC .. A61M 2005/3104; A61M 2005/3106; A61M 5/3146; A61M 5/31505; A61M 2005/3117; A61M 2205/0205; A61M 39/20; A61M 2039/0018; A61M 2039/0285; A61M 5/14; A61M 2005/1401; A61M 2005/1403; A61M 2039/0009; A61M 9/00; A61M 5/00; A61M 5/3129; A61M 5/34; A61M 39/165; A61M 2005/3118; A61M 2005/312; A61M 2005/31508
See application file for complete search history.

(56) References Cited

U.S. PATENT DOCUMENTS

| | | | |
|---|---|---|---|
| 4,597,758 A | 7/1986 | Aalto et al. | |
| 4,642,102 A | 2/1987 | Ohmori | |
| 4,711,363 A | 12/1987 | Marino | |
| 4,738,376 A | 4/1988 | Markus | |
| 4,906,231 A | 3/1990 | Young | |
| 5,084,017 A | 1/1992 | Maffetone | |
| 5,496,288 A | 3/1996 | Sweeny | |
| 5,676,406 A | 10/1997 | Simmons et al. | |
| 5,984,123 A | 11/1999 | Mogami et al. | |
| 6,565,529 B1 | 5/2003 | Kimber et al. | |
| 6,632,199 B1 * | 10/2003 | Tucker ............... | A61M 5/3134 604/192 |
| 7,083,605 B2 | 8/2006 | Miyahara | |
| 8,012,131 B2 | 9/2011 | Moser et al. | |
| 8,388,894 B2 | 3/2013 | Colantonio | |
| 8,647,308 B2 | 2/2014 | Solomon et al. | |
| 8,721,627 B2 | 5/2014 | Alpert et al. | |
| 8,777,504 B2 | 7/2014 | Shaw et al. | |
| 8,784,388 B2 * | 7/2014 | Charles ............... | A61M 39/162 604/199 |
| 9,132,223 B1 | 9/2015 | Wakeel | |
| 9,192,449 B2 | 11/2015 | Kerr et al. | |
| 9,399,125 B2 | 7/2016 | Burkholz | |
| 10,099,048 B2 | 10/2018 | Chiu et al. | |
| 10,166,381 B2 | 1/2019 | Gardner et al. | |
| 10,589,080 B2 | 3/2020 | Hitchcock et al. | |
| 10,603,481 B2 | 3/2020 | Avula et al. | |
| 2003/0093009 A1 | 5/2003 | Newby et al. | |
| 2003/0209681 A1 | 11/2003 | Leinsing et al. | |
| 2004/0039341 A1 | 2/2004 | Ranalletta | |
| 2005/0147525 A1 | 7/2005 | Bousquet | |
| 2007/0060904 A1 | 3/2007 | Vedrine et al. | |
| 2008/0171995 A1 | 7/2008 | Vitullo et al. | |
| 2008/0177250 A1 | 7/2008 | Howlett et al. | |
| 2009/0008393 A1 | 1/2009 | Howlett et al. | |
| 2009/0062766 A1 | 3/2009 | Howlett et al. | |
| 2010/0000040 A1 | 1/2010 | Shaw et al. | |
| 2010/0049170 A1 | 2/2010 | Solomon et al. | |
| 2010/0100056 A1 | 4/2010 | Cawthon et al. | |
| 2011/0046603 A1 | 2/2011 | Felsovalyi et al. | |
| 2011/0054440 A1 * | 3/2011 | Lewis ............... | A61M 39/16 604/506 |
| 2012/0039764 A1 | 2/2012 | Solomon et al. | |
| 2012/0123386 A1 | 5/2012 | Tsals | |
| 2012/0302997 A1 | 11/2012 | Gardner et al. | |
| 2013/0085474 A1 * | 4/2013 | Charles ............... | A61M 39/162 604/513 |
| 2013/0171030 A1 | 7/2013 | Ferlic et al. | |
| 2013/0197485 A1 | 8/2013 | Gardner et al. | |
| 2013/0033864 A1 | 12/2013 | Spinger et al. | |
| 2013/0338644 A1 | 12/2013 | Solomon et al. | |
| 2014/0052074 A1 * | 2/2014 | Tekeste ............... | A61M 5/31 604/199 |
| 2014/0148781 A1 | 5/2014 | Tekeste | |
| 2014/0150832 A1 | 6/2014 | Rogers et al. | |
| 2015/0094666 A1 | 4/2015 | Bates et al. | |
| 2017/0203092 A1 | 7/2017 | Ryan et al. | |
| 2018/0200145 A1 | 7/2018 | Sanders et al. | |
| 2018/0200500 A1 | 7/2018 | Ziebol et al. | |
| 2018/0243547 A1 | 8/2018 | Fox et al. | |
| 2018/0256883 A1 | 9/2018 | Follman et al. | |
| 2019/0151643 A1 | 5/2019 | Alpert | |
| 2019/0234540 A1 | 8/2019 | Marici et al. | |
| 2019/0308006 A1 | 10/2019 | Erekovcanski et al. | |
| 2019/0351212 A1 | 11/2019 | Dudar et al. | |
| 2020/0238070 A1 | 7/2020 | Ryan | |
| 2021/0187267 A1 | 6/2021 | Jiang | |

FOREIGN PATENT DOCUMENTS

| | | |
|---|---|---|
| CN | 103025374 A | 4/2013 |
| DE | 20017013 U1 | 12/2000 |
| DE | 10247963 A1 | 5/2004 |
| DE | 202005004079 U1 | 7/2006 |
| EP | 2606930 A1 | 6/2013 |
| EP | 2832391 B1 | 2/2015 |
| EP | 3275490 A1 | 1/2018 |
| GB | 2518646 A | 4/2015 |
| JP | 2016511111 A | 4/2016 |
| WO | 200024442 A1 | 5/2000 |
| WO | 200224551 A1 | 3/2002 |
| WO | 2011066586 A1 | 6/2011 |
| WO | 2014159346 A1 | 10/2014 |
| WO | 2015127285 A1 | 8/2015 |
| WO | 2017087400 A1 | 5/2017 |
| WO | 2017095373 A1 | 6/2017 |
| WO | 2018106508 A1 | 6/2018 |
| WO | 2019152482 A1 | 8/2019 |
| WO | 2019212637 A1 | 11/2019 |
| WO | 2020112767 A1 | 6/2020 |

OTHER PUBLICATIONS

PCT International Search Report and Written Opinion in PCT/US2020/015535 dated May 4, 2020, 13 pages.
Non-Final Office Action in U.S. Appl. No. 16/378,015, dated Oct. 30, 2020, 18 pages.
PCT International Search Report and Written Opinion in PCT/US2020/041312 dated Oct. 19, 2020, 11 pages.
PCT International Search Report and Written Opinion in PCT/US2020/044942 dated Oct. 16, 2020, 15 pages.
PCT International Search Report and Written Opinion in PCT/US2020/044951 dated Oct. 14, 2020, 14 pages.
Non-Final Office Action in U.S. Appl. No. 15/838,461 dated Jul. 24, 2020, 10 pages.
Non-Final Office Action in U.S. Appl. No. 16/253,683, dated Jun. 26, 2020, 9 pages.
PCT International Search Report and Written Opinion in PCT/US2020/041097 dated Oct. 27, 2020, 18 pages.
PCT International Search Report and Written Opinion in PCT/US2021/027214 dated Jul. 19, 2021, 14 pages.
PCT International Search Report and Written Opinion in PCT/US2021/027218 dated Jul. 22, 2021, 14 pages.
PCT International Search Report and Written Opinion in PCT/US2021/02722 dated Jul. 21, 2021, 15 pages.
PCT Invitation to Pay Additional Fees in PCT/US2021/01954, dated Jun. 15, 2021, 17 pages.
PCT Invitation to Pay Additional Fees in PCT/US2021/027219, dated Jul. 22, 2021, 15 pages.
Non-Final Office Action in U.S. Appl. No. 16/378,015, dated Mar. 30, 2021, 10 pages.
PCT International Search Report and Written Opinion in PCT/US2020/065229 dated Mar. 29, 2021, 12 pages.

(56) References Cited

OTHER PUBLICATIONS

Final Office Action in U.S. Appl. No. 16/253,683, dated Dec. 23, 2020, 9 pages.
PCT International Search Report and Written Opinion in PCT/US2020/057611 dated Feb. 5, 2021, 11 pages.
Non-Final Office Action in U.S. Appl. No. 17/076,102 dated Aug. 24, 2021, 10 pages.
PCT International Search Report and Written Opinion in PCT/US2021/027220 dated Jul. 21, 2021, 15 pages.
PCT Invitation to Pay Additional Fees in PCT/US2021/019546, dated Jun. 15, 2021, 17 pages.
PCT International Search Report and Written Opinion in PCT/US2021/027219 dated Oct. 22, 2021, 22 pages.

* cited by examiner

FLUSH SYRINGE WITH DISINFECTING FEATURE

CROSS-REFERENCE TO RELATED APPLICATIONS

This application claims priority under 35 U.S.C. § 119(e) to U.S. Provisional Application No. 62/622,640, filed Jan. 26, 2018, the disclosures of which are incorporated herein by reference in their entirety.

TECHNICAL FIELD

The present disclosure generally relates to syringe assemblies and particularly to syringe assemblies comprising a disinfectant loaded swap to ensure adherence to aseptic techniques for use in flush procedures for vascular access devices (VAD's).

BACKGROUND

Vascular access devices (VADs) are commonly used therapeutic devices, which include intravenous (IV) catheters. If not properly maintained or if exposed to a non-sterile environment, the VADs can become contaminated, sealed with blood clots or spread infection. To ensure VADs are used properly and do not become sealed or infected, protocols to ensure sterile practice have been developed. These protocols include sterilizing the VAD and flushing the catheter with a flush solution. Catheters are flushed using syringe assemblies filled with various fluids. In some cases, different fluids are injected sequentially in accordance with the protocol. For example, a saline solution followed by an anticoagulant such as heparin. The size of the syringe used to flush intravenous (I.V.) lines varies by various factors including the size and length of the catheter. Typically syringes of 1 ml, 3 ml, 5 ml and 10 ml volume are used. VAD protocols usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections.

Conventional flush syringes have a barrel with a luer tip at one end which is exposed to the non-sterile environment once the syringe tip is removed from packaging thus providing an opportunity for undesired contamination.

Current "recommended practice" for aseptic IV line maintenance and IV drug delivery practices require adherence to a stepwise process referred to as "SASH." During the first step of the process, the clinician cleans/disinfects (generally with an alcohol swab) the VAD connector. Second, a syringe containing saline is used to flush the IV line or catheter (Saline flush), and then the VAD connector is disinfected a second time. Third, the fluid or pharmaceutical therapy is administered through the IV line or catheter (Administer therapy), the VAD connector is disinfected a third time, followed by a second Saline flush step. The final step, which is dependent upon the patient's need and institutional policy, is a final disinfection of the VAD connector followed by a Heparin lock step, where a small amount of heparin is injected into the IV line or catheter to prevent the formation of thrombi or blood clots. At the conclusion of this tedious stepwise process, the inlet port of the VAD connector is left exposed to the environment. This "recommended practice" requires disinfecting the VAD connector after each access makes IV line maintenance a very burdensome and time consuming process. Because the process is so cumbersome, clinicians very rarely implement this "recommended practice" in its entirety, and, thus, patients are exposed to the risk of contracting CRBSIs. Microorganisms populate exposed connector inlet surfaces, and, when the "recommended practice" is not adhered to, the microorganisms can enter the IV line during flushing. Furthermore, blood reflux into the IV line or catheter can cause clot formation inside the lines, and microorganisms from the connector inlet surfaces can colonize blood clots inside the lines and infect the patients during flushing.

There is a need, therefore, for a flush syringe assembly that promotes compliance with aseptic technique by eliminating the additional swabbing and disinfecting steps.

SUMMARY

One aspect of the present disclosure pertains to a flush syringe assembly including a barrel including a side wall having an inside surface defining a chamber for retaining a fluid, an open proximal end, a distal end including a distal wall with an elongate tip extending distally therefrom having a passageway therethrough in fluid communication with said chamber. A collar may extend from the distal wall of the barrel and surrounding the elongate tip, the collar including at least one side wall having an inside surface defining a compartment, an open distal end, a proximal end adjacent the distal wall of the barrel. A disinfectant-loaded swab may be disposed in the collar. An elongated plunger rod may be disposed within the barrel, the plunger rod comprising a distal end and a proximal end, the distal end including a stopper slidably positioned in fluid-tight engagement with the inside surface of the barrel for drawing fluid into and driving fluid out of the chamber by movement of the stopper relative to the barrel, the elongated plunger rod extending outwardly from the open proximal end of the barrel, the stopper having a distal surface.

In one or more embodiments, the fluid is a flush fluid.

In one or more embodiments, the disinfectant-loaded swab has one or more openings or slits on a top surface of the swab.

In one or more embodiments, the compartment of the collar surrounds the elongate tip.

Another aspect of the present disclosure pertains to a flush syringe assembly comprising a barrel including a side wall having an inside surface defining a chamber for retaining a fluid, an open proximal end, a distal end including a distal wall with an elongate tip extending distally therefrom having a passageway therethrough in fluid communication with said chamber. A collar extending from the distal wall of the barrel and surrounding the elongate tip, the collar including at least one side wall having an inside surface defining a compartment, an open distal end, a proximal end adjacent the distal wall of the barrel. A disinfectant-loaded swab may be disposed in the collar. A removable cap having a body, a proximal end, and a closed distal end, the removable cap being mounted on the distal end of the collar. An elongated plunger rod may be disposed within the barrel, the plunger rod comprising a distal end and a proximal end. A stopper slidably may be disposed on the distal end of the plunger rod and positioned in fluid-tight engagement with the inside surface of the barrel for drawing fluid into and driving fluid out of the chamber by movement of the stopper relative to the barrel.

In one or more embodiments, the compartment of the collar surrounds the elongate tip.

In one or more embodiments, the distal wall of the collar includes a plurality of threads to connect the collar to the removable cap.

In one or more embodiments, the fluid is a flush fluid.

In one or more embodiments, the removable cap includes an outward protrusion extending from the body of the removable cap and corresponding with the passageway on the distal end of the elongate tip.

In one or more embodiments, the removable cap has a cross-sectional shape that is triangular, square, pentagonal, hexagonal, heptagonal, octagonal, symmetric or non-symmetric polygonal.

In one or more embodiments, the collar has a cross-sectional shape that is triangular, square, pentagonal, hexagonal, heptagonal, octagonal, symmetric or non-symmetric polygonal.

In one or more embodiments, the disinfectant-loaded swab is made of an absorbent material.

In one or more embodiments, the disinfectant or antimicrobial agent may be ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

DETAILED DESCRIPTION

Figure 1:
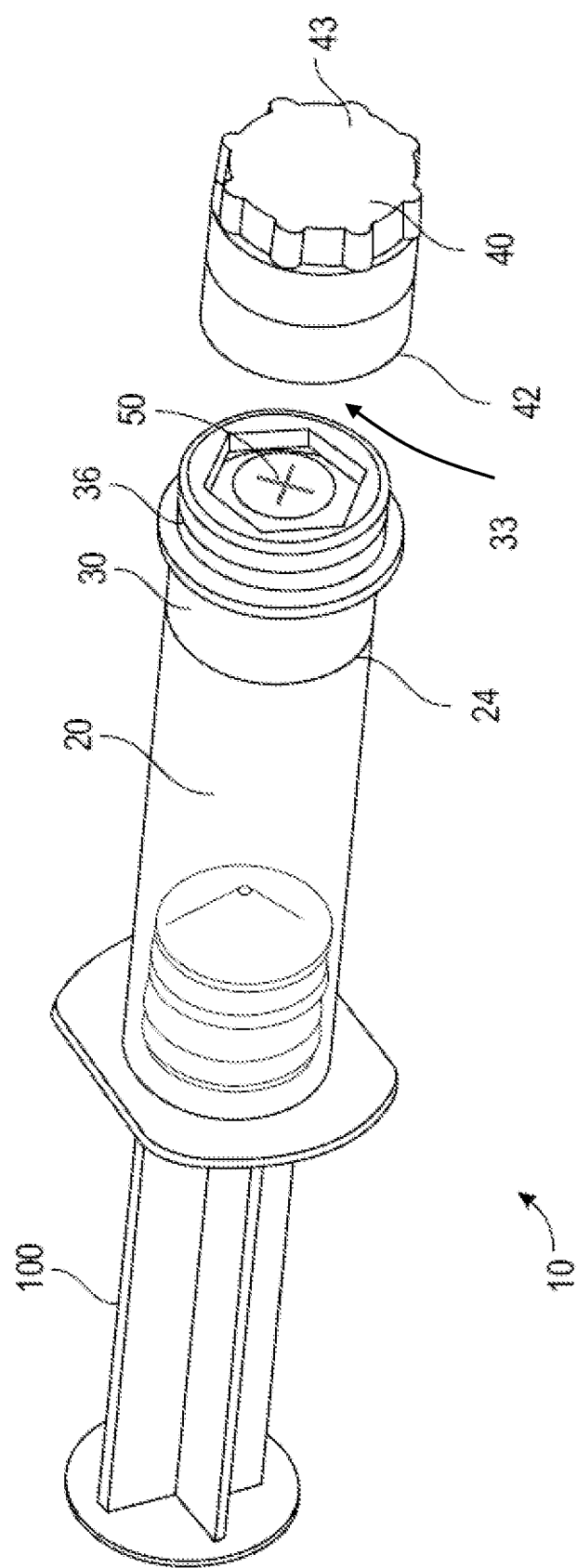
FIG. 1 illustrates a perspective view of a flush syringe with a collar and cap in accordance with one or more embodiments of the present disclosure.
Figure 2A:
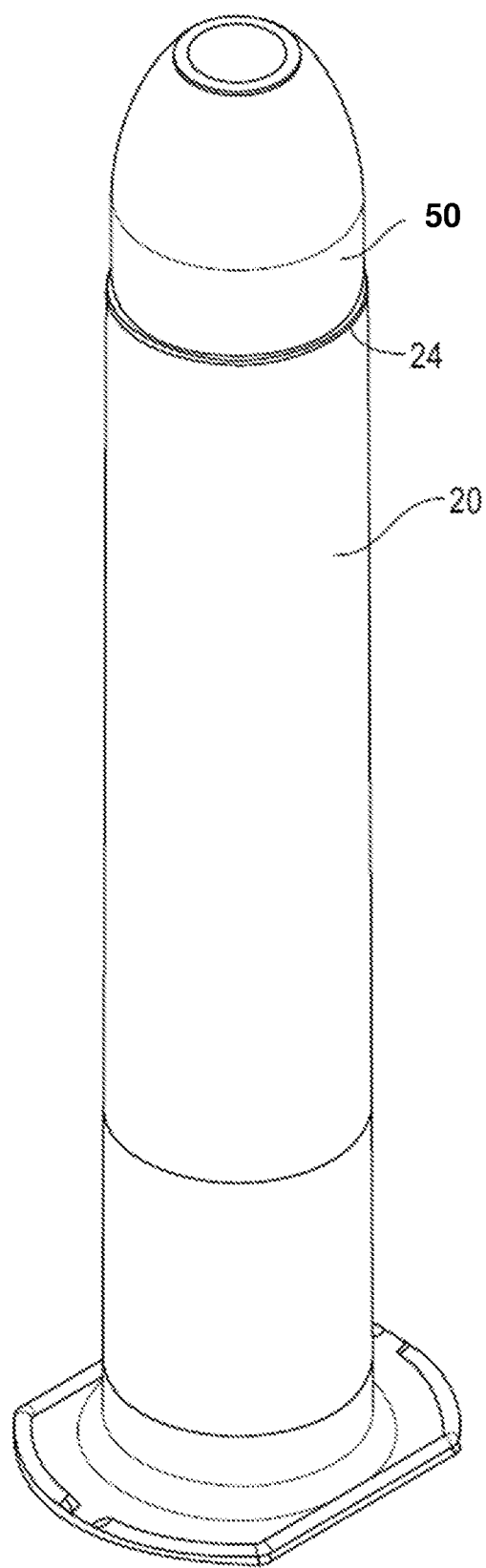
FIG. 2A illustrates a perspective view of a disinfectant-loaded swab that buckles in accordance with one or more embodiments of the present disclosure.
Figure 2B:
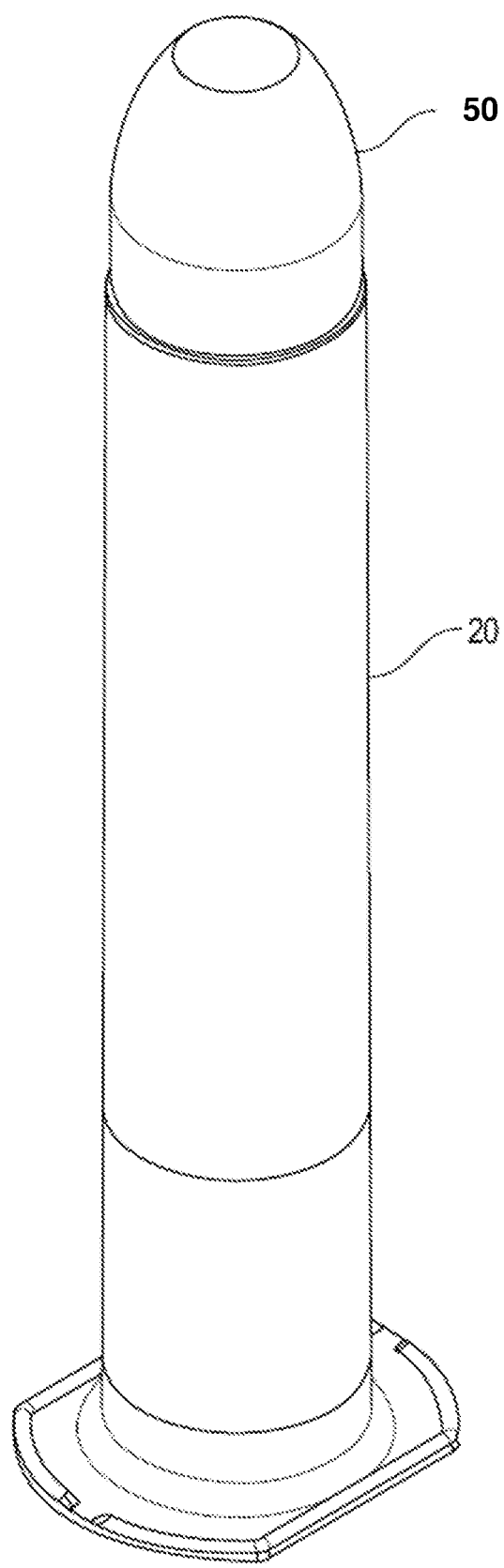
FIG. 2B illustrates a perspective view of an disinfectant-loaded swab that buckles in accordance with one or more alternate embodiments of the present disclosure.

Before describing several exemplary embodiments of the present disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

Reference to "flush syringe assembly" includes syringes that are indicated for use in the flushing of VADs. The practice of flushing ensures and maintains catheter patency and helps prevent the mixing of incompatible pharmaceuticals.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "microorganism" refers to a microbe or organism that is unicellular or lives in a colony of cellular organisms. Microorganisms are very diverse; they include, but are not limited to bacteria, fungi, archaea, and protozoans. Microorganisms are often the cause of CRBSIs. The most common microorganisms associated with CRBSIs include, but are not limited to, *Staphylococcus aureus* and *epidermis*, *Enterococcus faecalis*, *Escherichia coli*, *Pseudomonas aeruginosa*, and *Candida albicans*.

As used herein, the terms "antimicrobial agent" or "antimicrobial" refers to substances that kill or inhibit the growth of microorganisms such as bacteria, fungi, archaea, or protozoans. Antimicrobial agents either kill microbes, or prevent the growth of microbes.

As used herein, the term "disinfectant" refers to antimicrobial substances that are used on non-living objects or outside the body, e.g., on the skin.

In one or more embodiments, disinfectants or antimicrobial agent include, but are not limited to, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

As used herein, the term "absorbent material" refers to a material having capacity or tendency to absorb or soak up another substance. In one or more embodiments, the absorbent material has a tendency to absorb a disinfectant or antimicrobial. Absorbent materials may include sponges, absorbent cottons As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the VAD. A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Clinical best practice requires that clinicians disinfect the needleless connector with an alcohol swab, disinfectant cap, etc. before each flush, drug, and lock syringe, requiring the clinician to perform the disinfecting process multiple times for each catheter line access. In practice, there are low (40-45%) compliance rates to this disinfecting protocol. Embodiments of the present disclosure provide the advantage of increased and enforced compliance with the need to disinfect needless connectors which ultimately reduces the chances of hospital acquired infections. Use of embodiments of syringe assemblies disclosed in the present disclosure will require the clinician to open fewer packages and does not require the clinician to carry alcohol swabs. Moreover, use of embodiments of syringe assemblies disclosed in the present disclosure results in the combination of two existing steps into one step, thus simplifying workflow for the clinician. Embodiments of the present disclosure pertain to prefilled flush or lock syringes with an integrated swab that combines the two steps of disinfecting the hub and connecting the syringe into one, thus greatly improving compliance to best practices.

Provided are syringe assemblies that include a plunger rod and a syringe barrel having an open proximal end and a distal tip, the distal syringe tip surrounded by a collar that extends from the distal wall of the syringe barrel to form a compartment to house a disinfectant-loaded swab. The collar also facilitates alignment of the syringe with a catheter hub or needle-free connector, as well as, reducing contamination of the syringe by preventing contact of the syringe tip with the surrounding non-sterile environment.

Referring to FIGS. 1-44, a syringe assembly 10 according to the present disclosure generally comprises a barrel 20, including a side wall 21 having an inside surface defining a chamber 22 for retaining a fluid. In one or more embodiments, the fluid is a flush fluid. The barrel 20 further includes an open proximal end and a distal end 24 having a distal wall 25. A collar 30 extends from the distal wall 25 of the syringe barrel 20 to form a compartment 33 to house a disinfectant-loaded swab 50. In one or more embodiments, the collar 30 and swab 50 surrounds an elongated tip 26 and an outer rim 28 extending distally from the distal wall 25 of the barrel 20. The elongated tip 26 having a passageway 27 therethrough in fluid communication with the chamber 22, the collar extending from the distal wall 25 of the barrel to surround the elongated tip 26. In a further embodiment, the collar 30 surrounds an elongate tip 26 adapted for connection to the hub of the vascular access devices, wherein the tip 26 is a luer tip having the outer rim 28 of threading.

Figure 17:
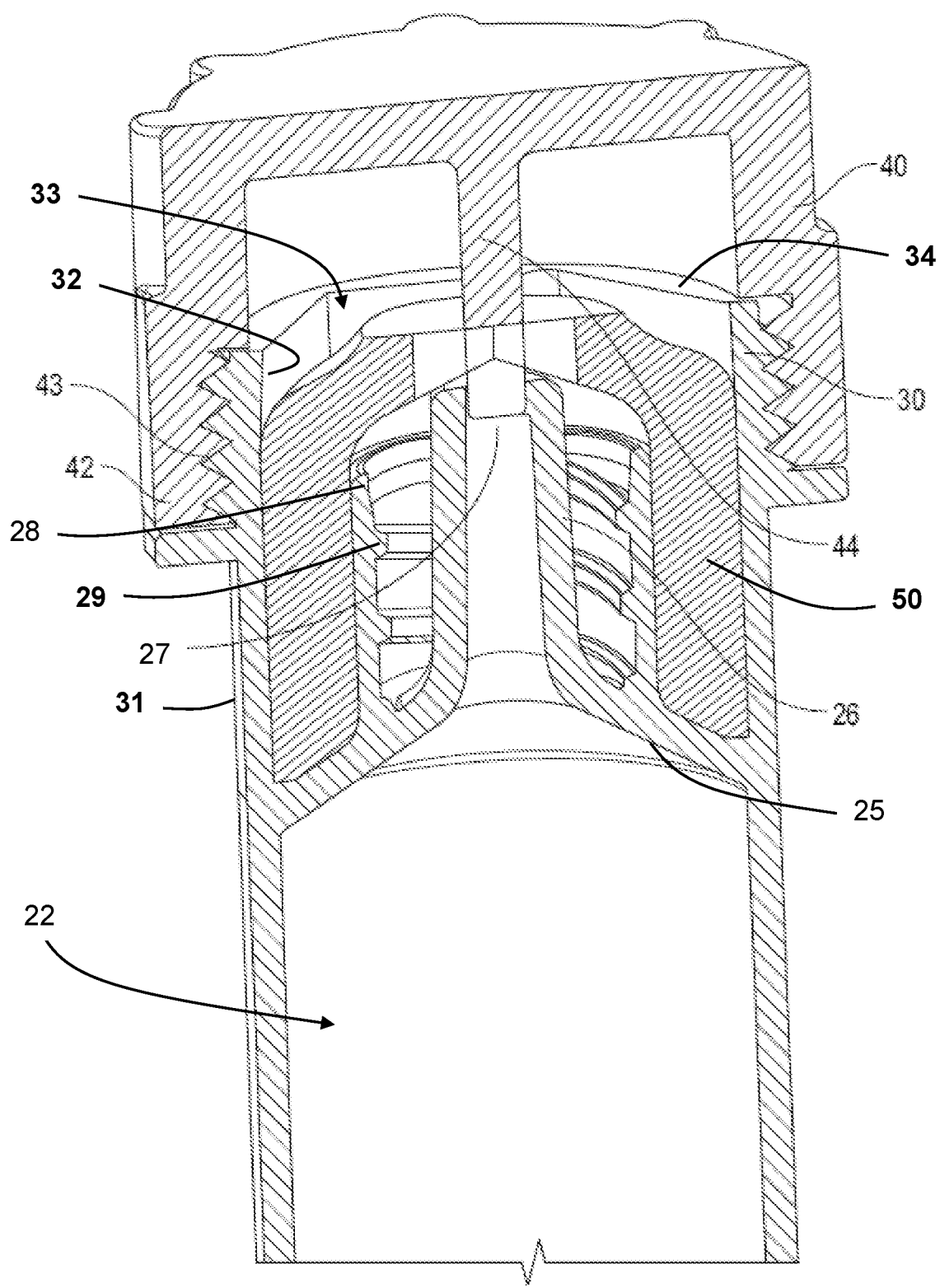
FIG. 17 illustrates a cross-sectional view of a flush syringe with a collar and a cap in accordance with one or more embodiments of the present disclosure.

As shown in FIGS. 1 and 17, collar 30 is disposed on the distal end 24 of the barrel, the collar 30 including at least one side wall 31 having an inside surface 32 defining a compartment 33 surrounding the elongated tip 26 and the outer rim 28, a open distal end 34, and a proximal end 35 adjacent the distal wall 25 of the barrel. In one or more embodiments, compartment 33 houses the disinfectant-loaded swab 50. The open distal end 34 of the collar 30 may comprise a plurality of threads 36 on the inside surface or outside surface for attachment to a removable cap 40. Elongated tip 26 may be adapted for connection to a hub of a vascular access device. The outer rim 28 may comprise a plurality of threads 29 on the outside surface or inside surface for connection to a vascular access device. The shape of the swab 50 can vary. Swab 50 may have shapes including, but not limited to, a convex inner surface (for example a paraboloid), concave inner surface, with a straight profile (i.e., semi conical shape), or have the shape of a trapezoidal prism. The length of this extension from the main body of syringe and the degree of openness/straightness of the profile (how wide the collar is at the end farthest from the syringe barrel) can vary.

In an embodiment, the outer rim 28 may comprise a plurality of threads 29 adapted for connection to the hub of the vascular access device. In one or more embodiments, the outer rim 28 surrounds an elongate tip adapted for connection to the hub of the vascular access devices. In one or more embodiments, the elongate tip 26 is a luer tip.

Disinfectant-loaded swab 50 may comprise an absorbent material for soaking up the disinfectant or antimicrobial agent that is housed within the compartment 33. The disinfectant or antimicrobial agent can be a fluid or a gel selected from the group consisting of selected from the group consisting of IPA, ethanol, chlorhexidine, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, and mixtures thereof. The disinfectant or antimicrobial agent can be a fluid or a gel.

In one or more embodiments, disinfectant-loaded swab 50 has one or more openings or slits 51 on the top surface to allow a needleless connector to go through to connect to the elongate tip 26. The disinfectant-loaded swab 50 will deform in way so as to create sufficient friction and scrubbing between the VAD connector and disinfectant-loaded swab 50, and to release the disinfectant as it gets compressed in order to disinfect the needleless connector surfaces. Following full engagement of the syringe assembly and VAD connector, the fluid in the chamber of the syringe barrel 20 can be administered.

As shown in FIGS. 1 and 17, shows an assembly having a barrel 20, collar 30 engaged to removable cap 40, which houses a disinfectant-loaded swab 50 that buckles when connected to a syringe tip.

Figure 3:
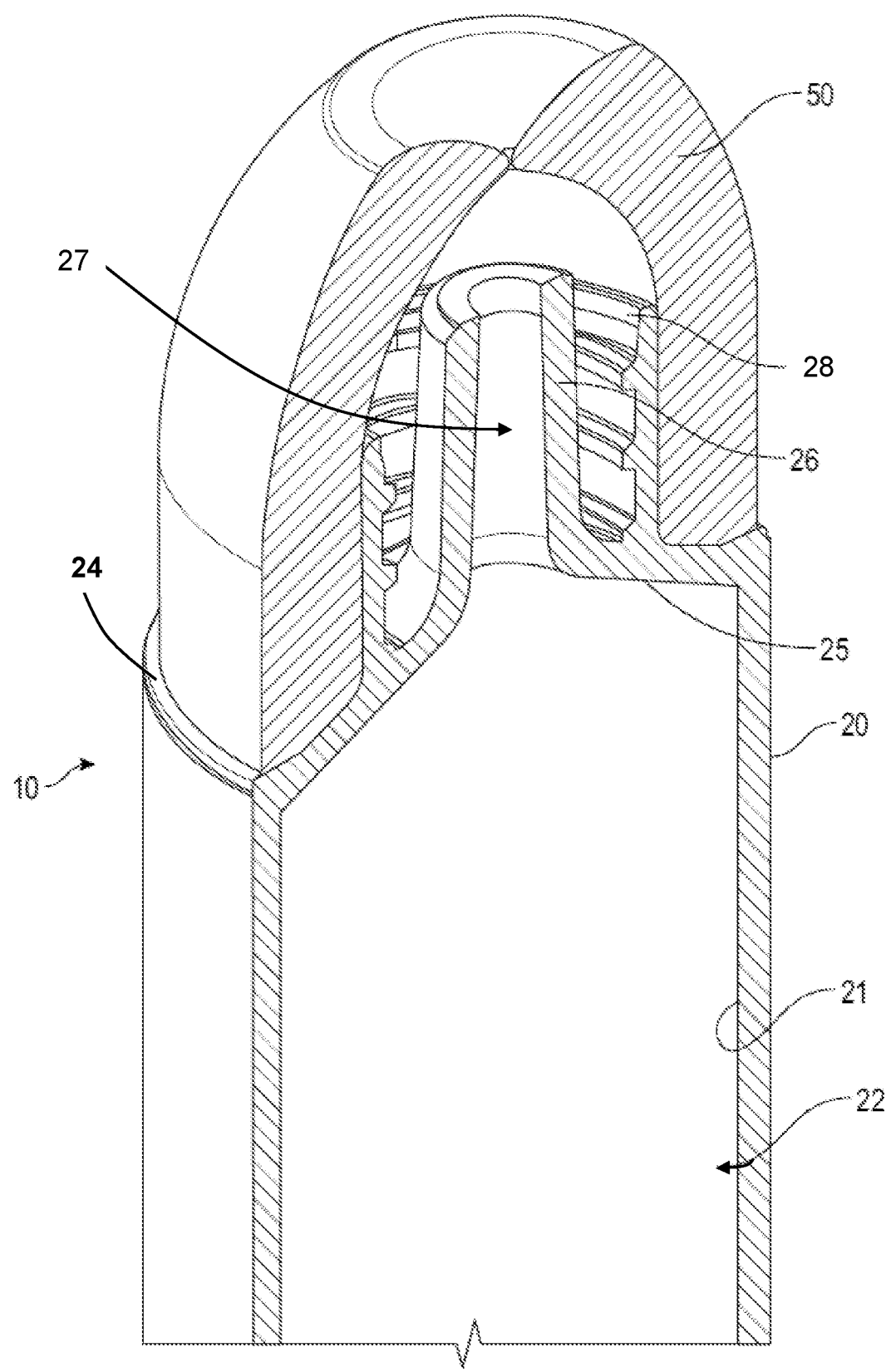
FIG. 3 illustrates a cross sectional view of a flush syringe with a disinfectant-loaded swab in accordance with one or more embodiments of the present disclosure.
Figure 4:
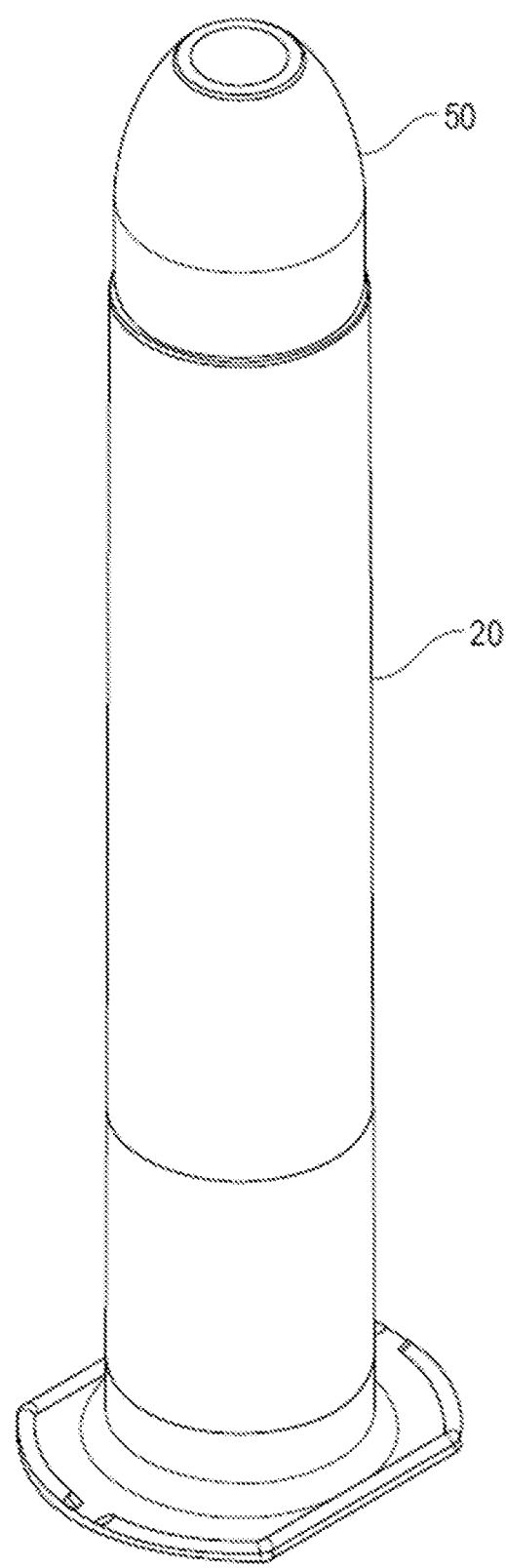
FIG. 4 illustrates a perspective view of a flush syringe of FIG. 3 in accordance with one or more embodiments of the present disclosure.

FIGS. 3 and 4 show a cross-sectional and perspective view of a flush syringe having a dome or frusto-conical shaped disinfectant-loaded swab 50 with a dimpled top having a sidewall that has a uniform thickness in accordance with one or more embodiments of the present disclosure.

Figure 5:
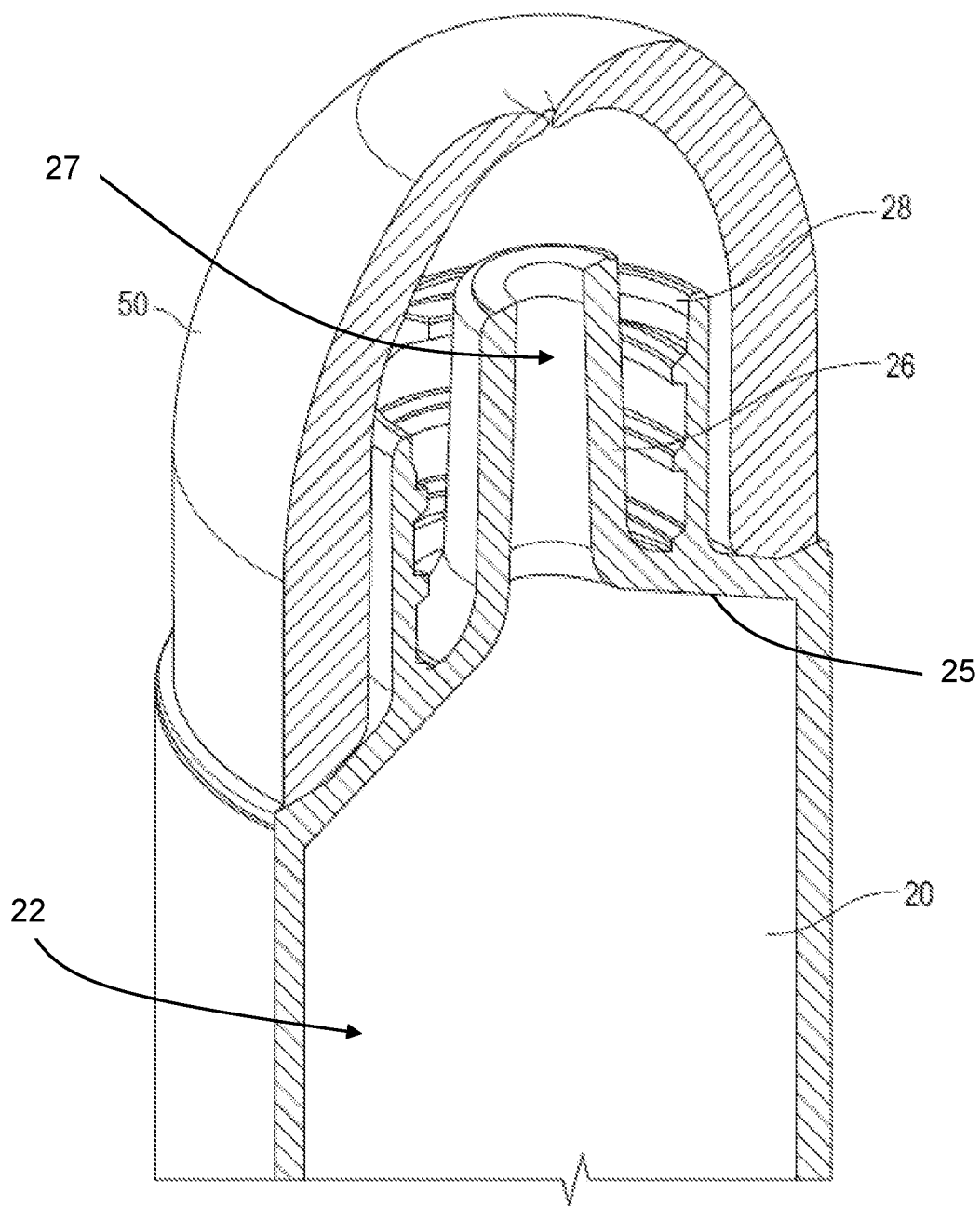
FIG. 5 illustrates a cross sectional view of a flush syringe with a disinfectant-loaded swab in accordance with one or more alternate embodiments of the present disclosure.
Figure 6:
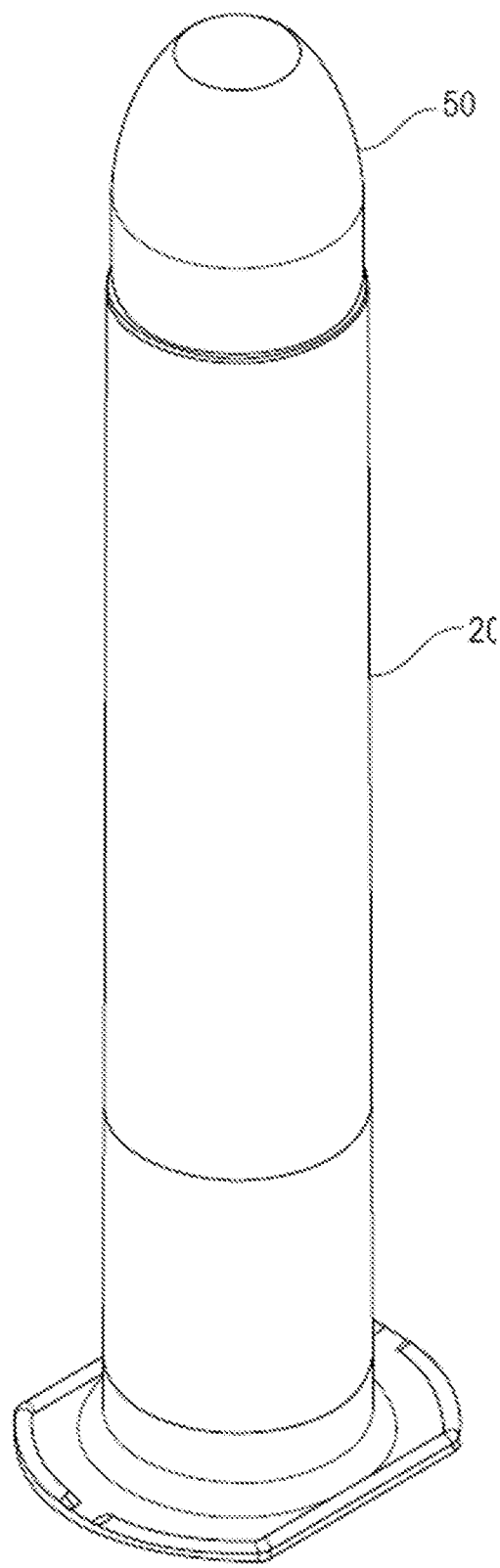
FIG. 6 illustrates a perspective view of a flush syringe of FIG. 5 in accordance with one or more embodiments of the present disclosure.

FIGS. 5 and 6 show a cross-sectional and perspective view of an alternate flush syringe in accordance with one or more embodiments of the present disclosure having a frusto-conical shaped disinfectant-loaded swab 50 with a dimpled top having a sidewall that has a tapered thickness wherein the sidewall at the dimpled top of the swab 50 is less thick than the sidewall at the base of the swab 50.

Figure 7:
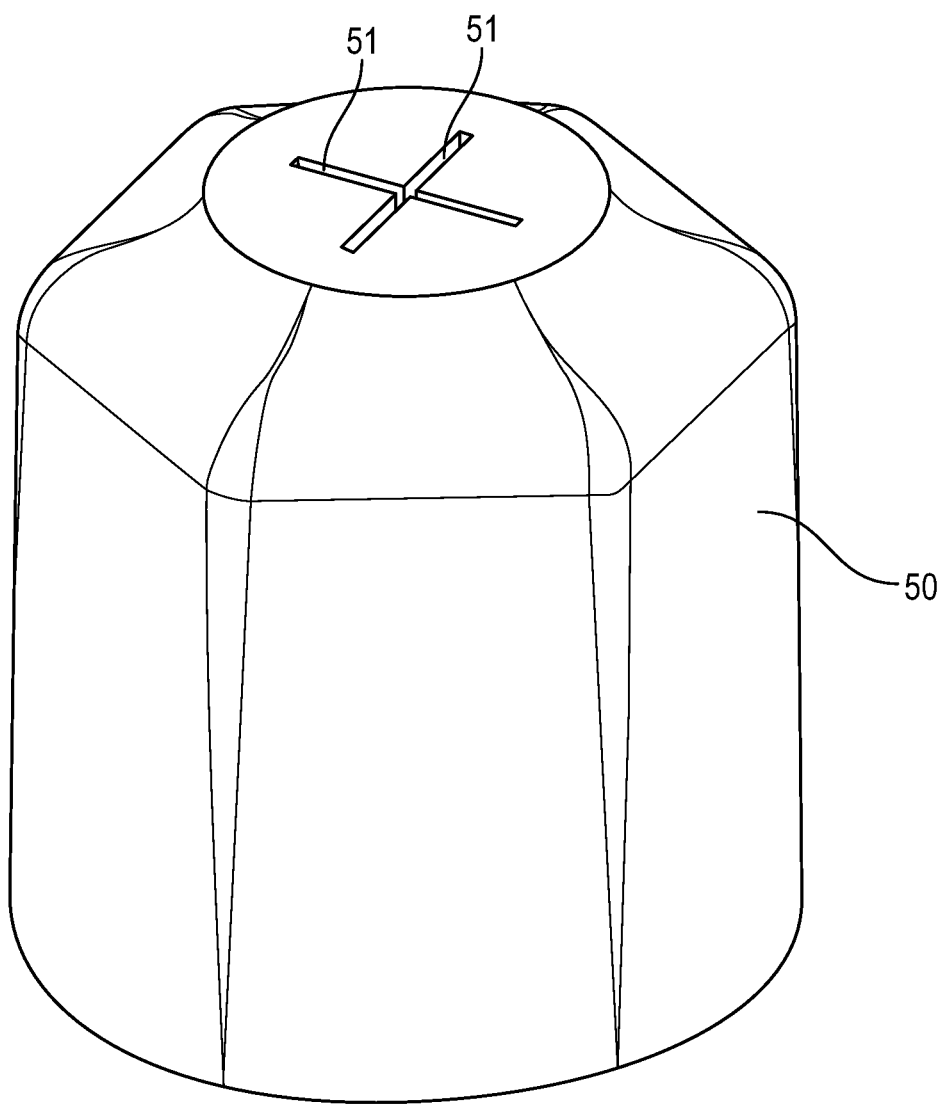
FIG. 7 illustrates a perspective view of a hexagonal shaped disinfectant-loaded swab having two slits in accordance with one or more embodiments of the present disclosure.

FIG. 7 shows a hexagonal shaped disinfectant-loaded swab 50 having two slits 51 in a cross shape with a center opening at the intersection of slits 51 in accordance with one or more embodiments of the present disclosure.

Figure 8:
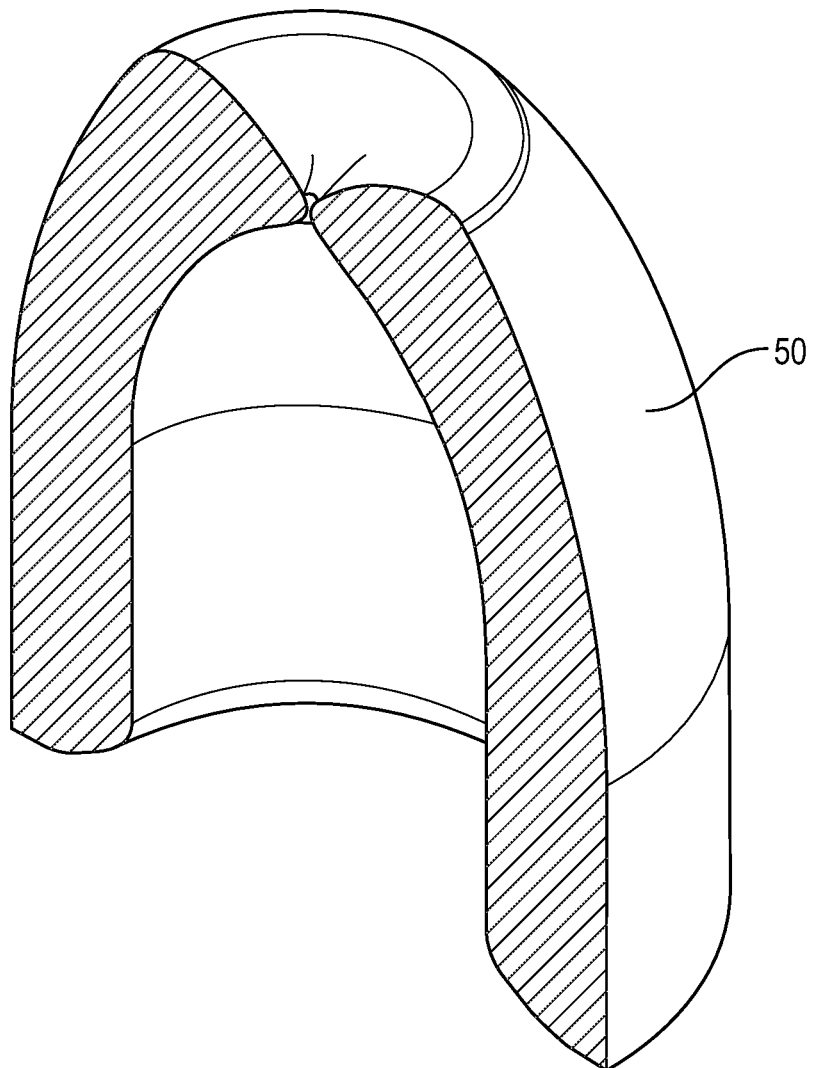
FIG. 8 illustrates a cross sectional view of a swab in accordance with one or more embodiments of the present disclosure.
Figure 9:
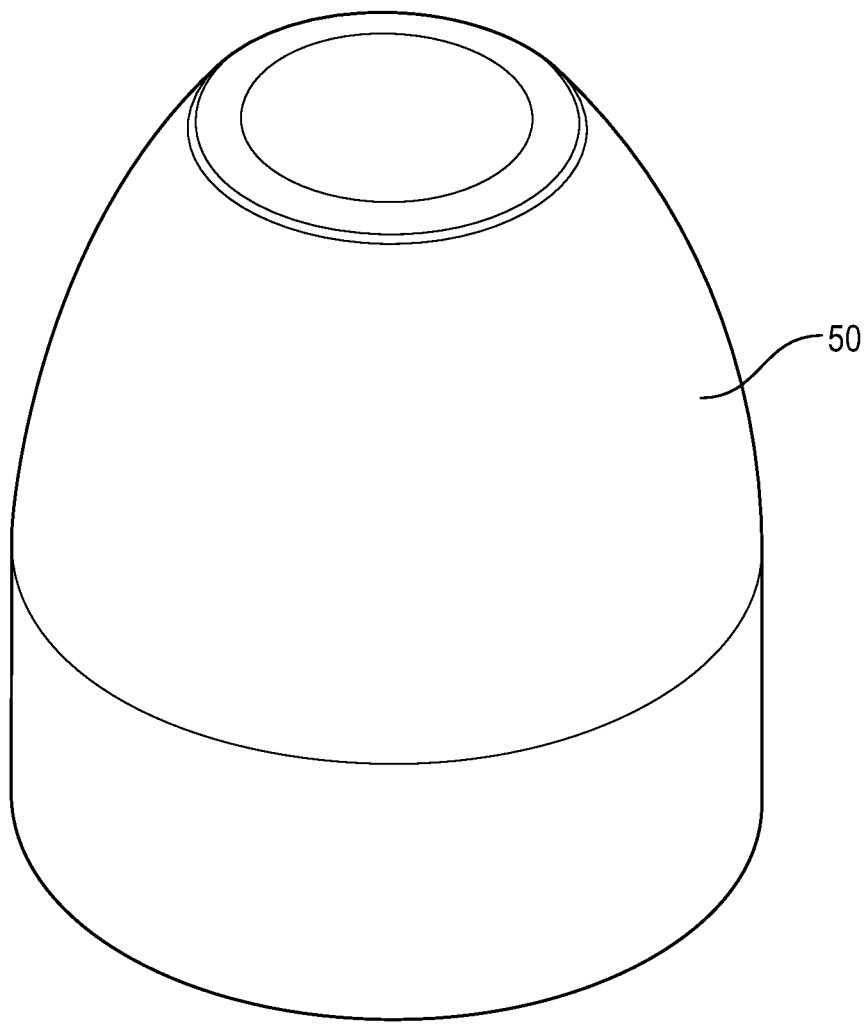
FIG. 9 illustrates a perspective view of a swab in accordance with one or more embodiments of the present disclosure.

As shown in FIG. 8, an alternate swab 50 may include a dome-shaped swab with a flat rim top that tapers or funnels toward a dimple or opening disposed in the center of the top of the swab in accordance with one or more embodiments of the present disclosure;

As shown in FIG. 9, an alternate swab 50 may include a dome-shaped swab with a flat top in accordance with one or more embodiments of the present disclosure.

Figure 10:
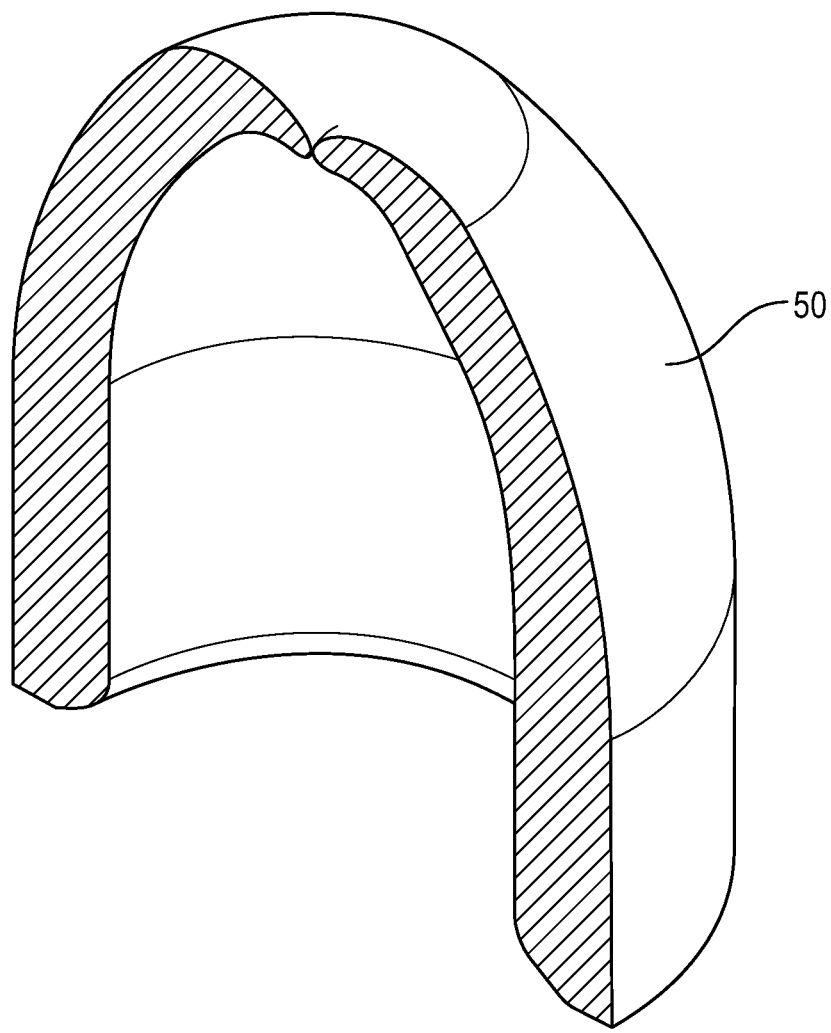
FIG. 10 illustrates cross section view of alternate swab in accordance with one or more embodiments of the present disclosure.
Figure 11:
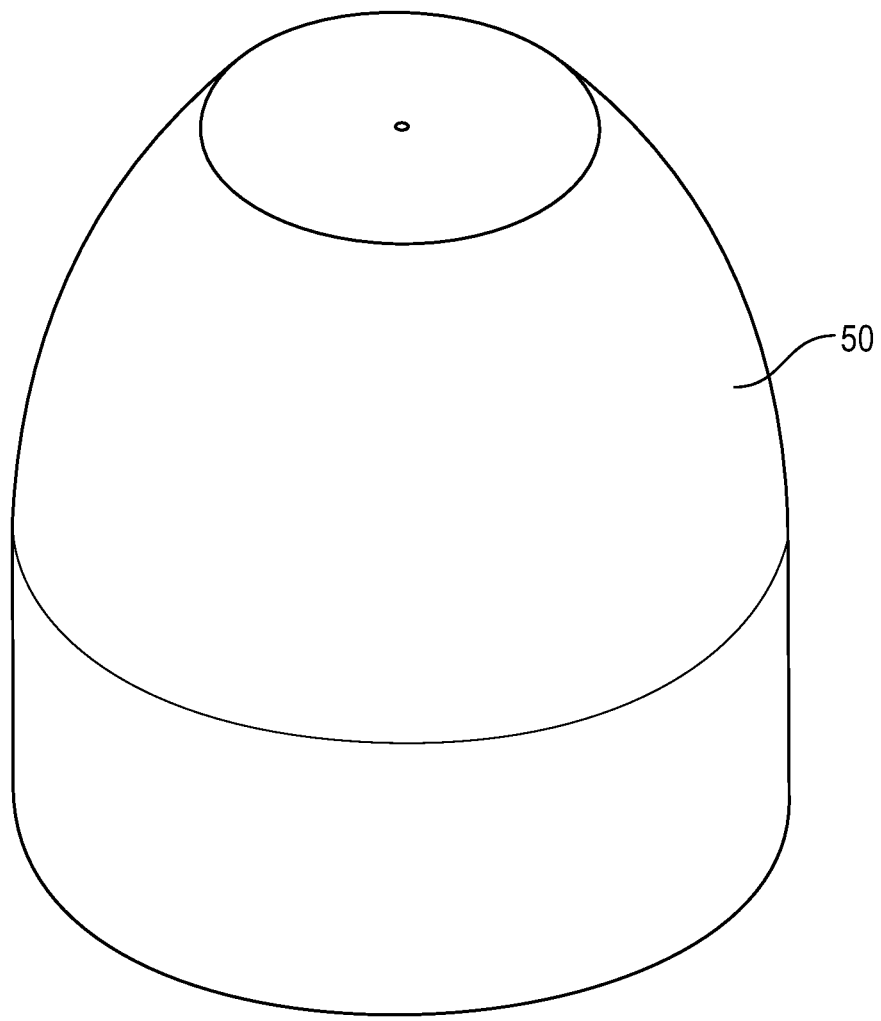
FIG. 11 illustrates a perspective view of a disinfectant-loaded swab in accordance with one or more embodiments of the present disclosure.
Figure 12:
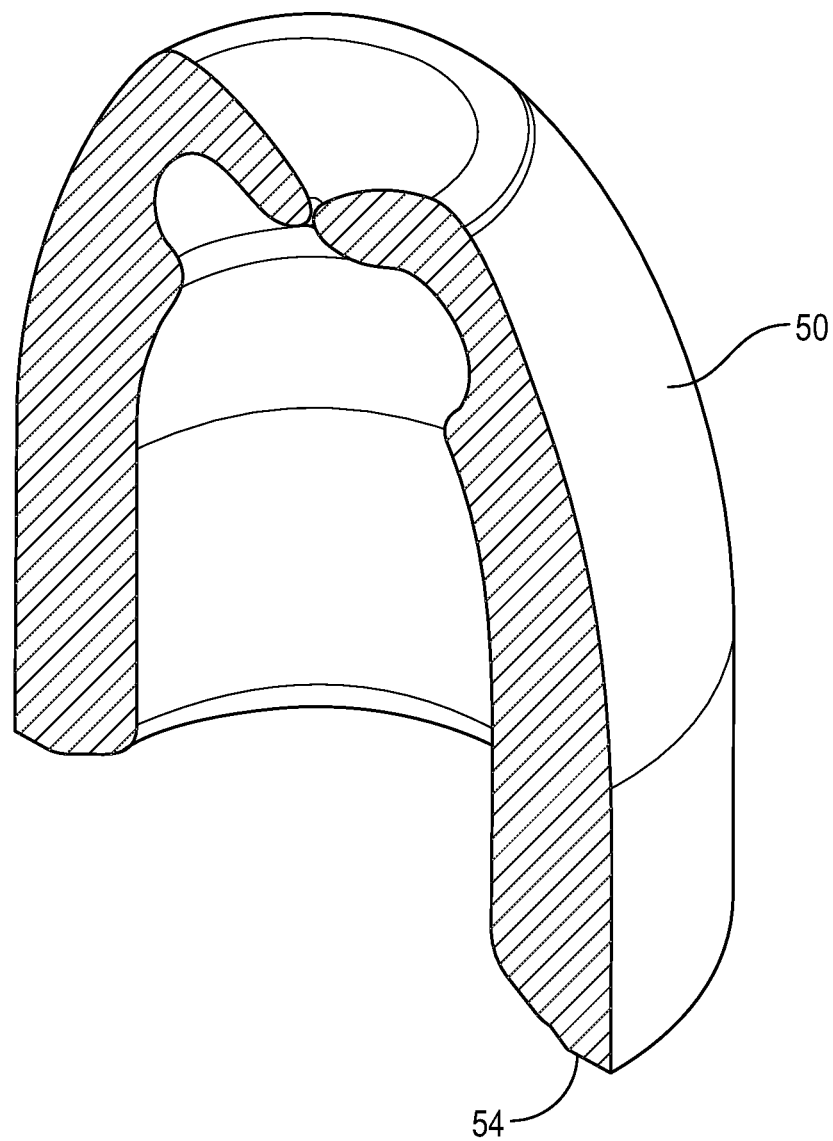
FIG. 12 illustrates a cross-sectional view of an alternate swab in accordance with one or more embodiments of the present disclosure.

As shown in FIG. 10, an alternate swab 50 may include a frusto-conical or dome-shaped top with a center dimple in accordance with one or more embodiments of the present disclosure;

FIGS. 11 and 12 illustrate a perspective view of a disinfectant-loaded swab 50 in accordance with one or more embodiments of the present disclosure. As shown in FIG. 12, an alternate swab 50 has a sidewall of varying thickness that forms one or more recess in the sidewall 54 of the swab to allow for buckling upon connection with a medical connector in accordance with one or more embodiments of the present disclosure.

Figure 13:
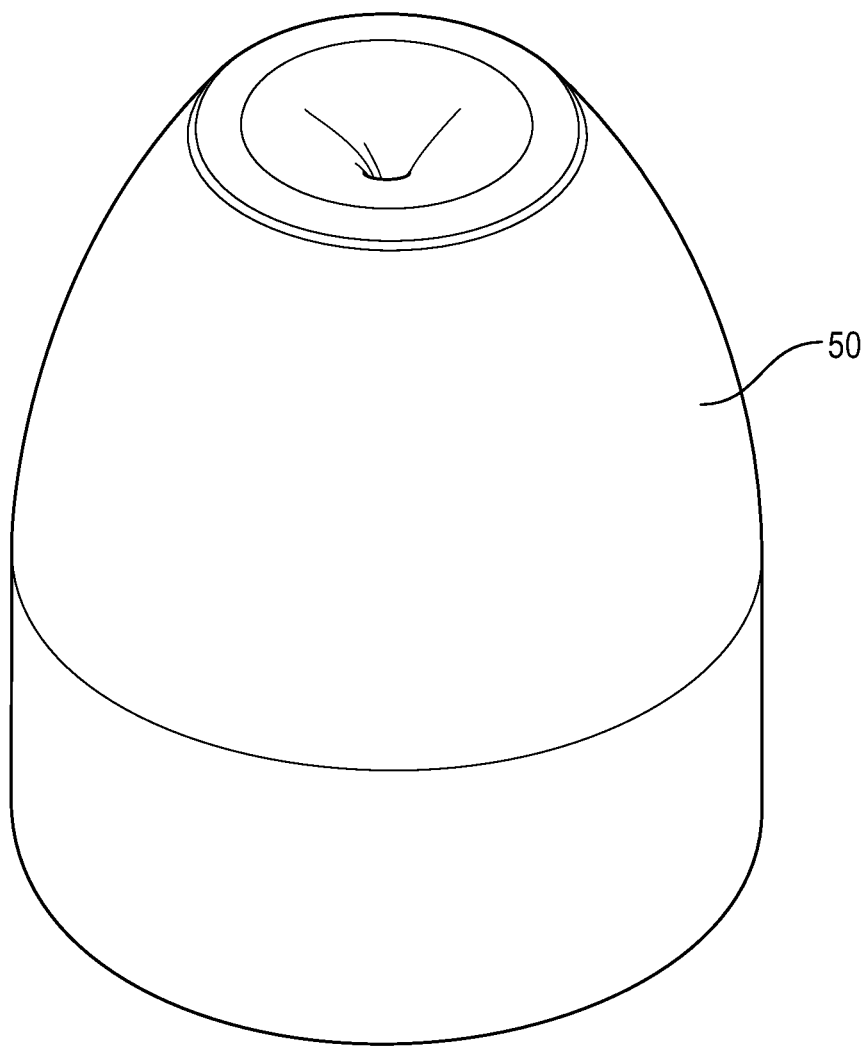
FIG. 13 illustrates a perspective view of a swab that buckles in accordance with one or more embodiments of the present disclosure.
Figure 14:
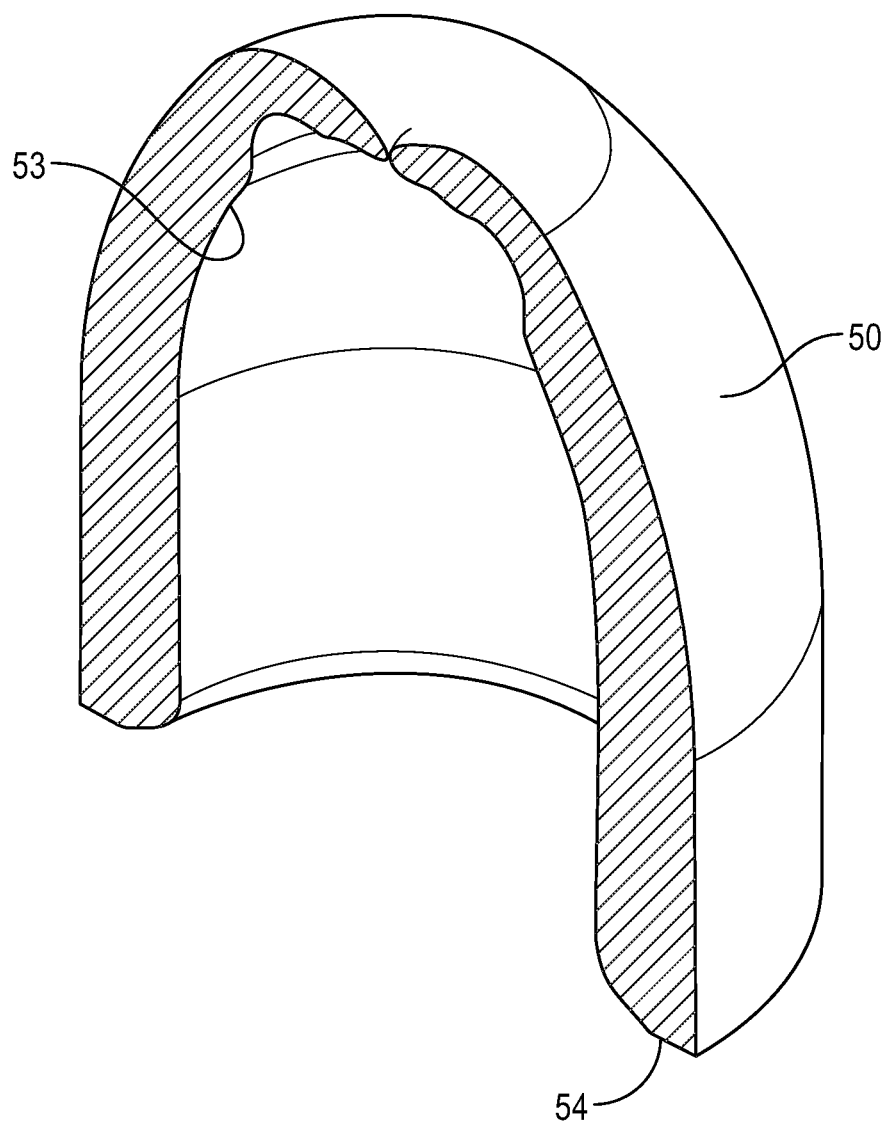
FIG. 14 illustrates a cross-sectional view of a swab that buckles in accordance with one or more embodiments of the present disclosure.
Figure 15:
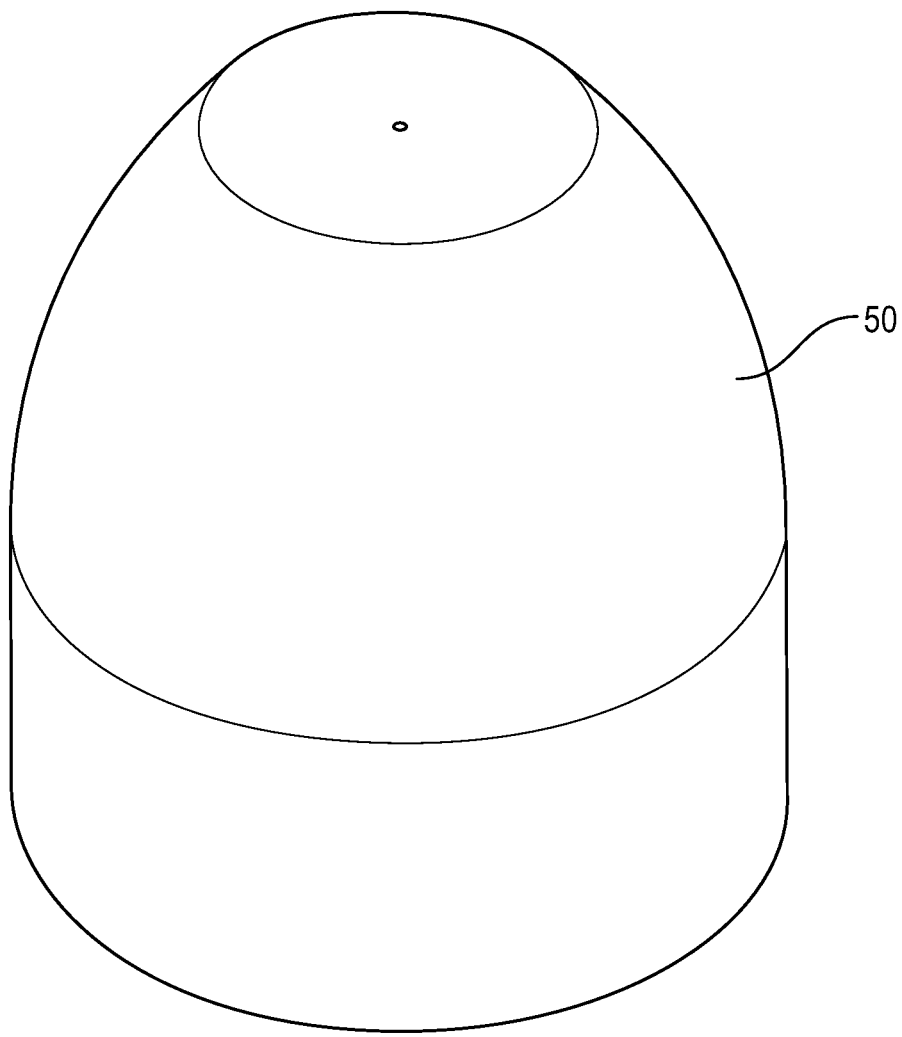
FIG. 15 illustrates a perspective view of a swab that buckles in accordance with one or more embodiments of the present disclosure.

As shown in FIGS. 13-15, alternate embodiments of a disinfectant-loaded swab 50 having an inner surface 53 with varying thickness, tapers, cut-out or recess in the sidewall 54 of the swab to allow for the disinfectant-loaded swab 50 to buckle and fold on itself and allow the penetration of needleless connector.

Figure 16:
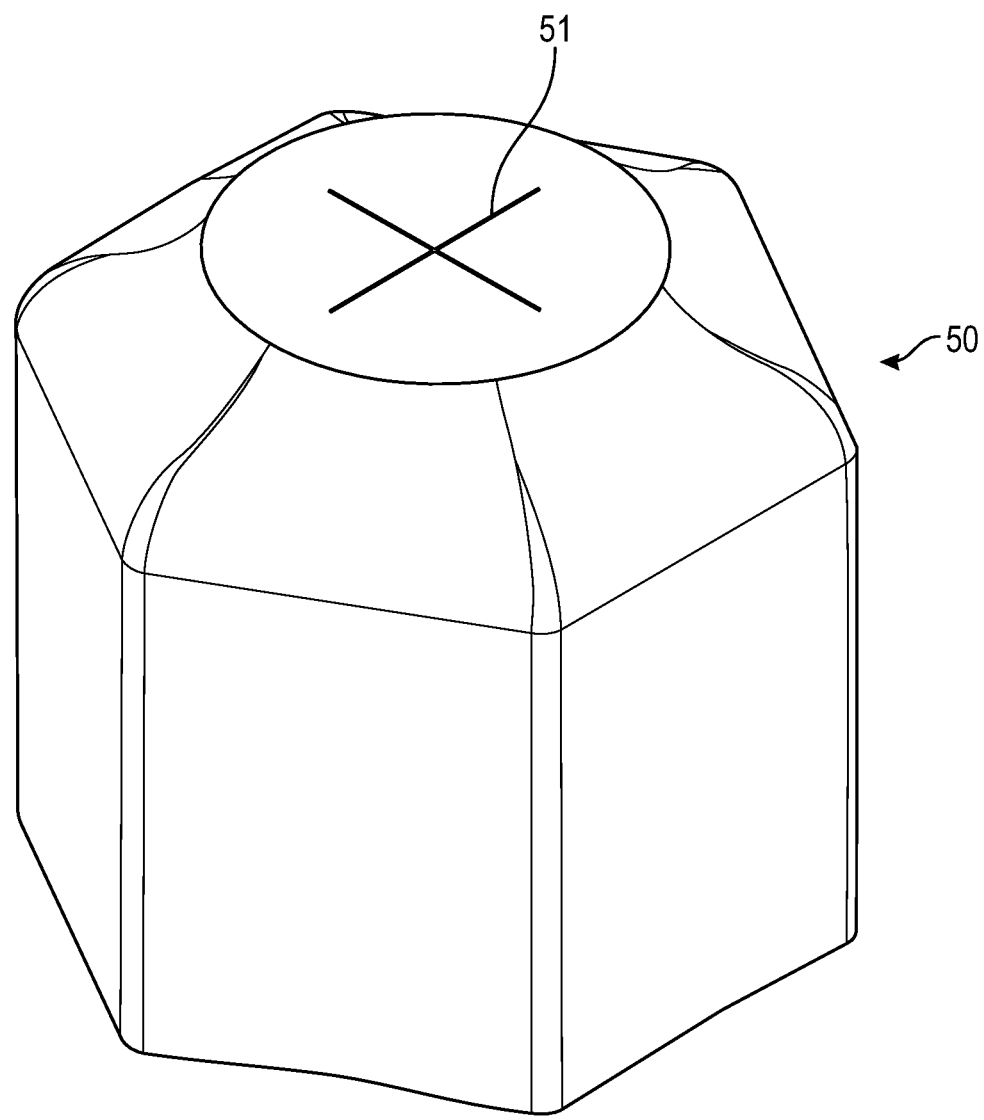
FIG. 16 illustrates a perspective view of a disinfectant-loaded swab in accordance with one or more embodiments of the present disclosure.

As shown in FIG. 16, a disinfectant-loaded swab 50 may have a sidewall that is hexagonal in shape that is tapered from the base to the top having a flat top with two slits 51 forming a cross-shaped opening at the top portion of the swab that in accordance with one or more embodiments of the present disclosure.

Figure 20:
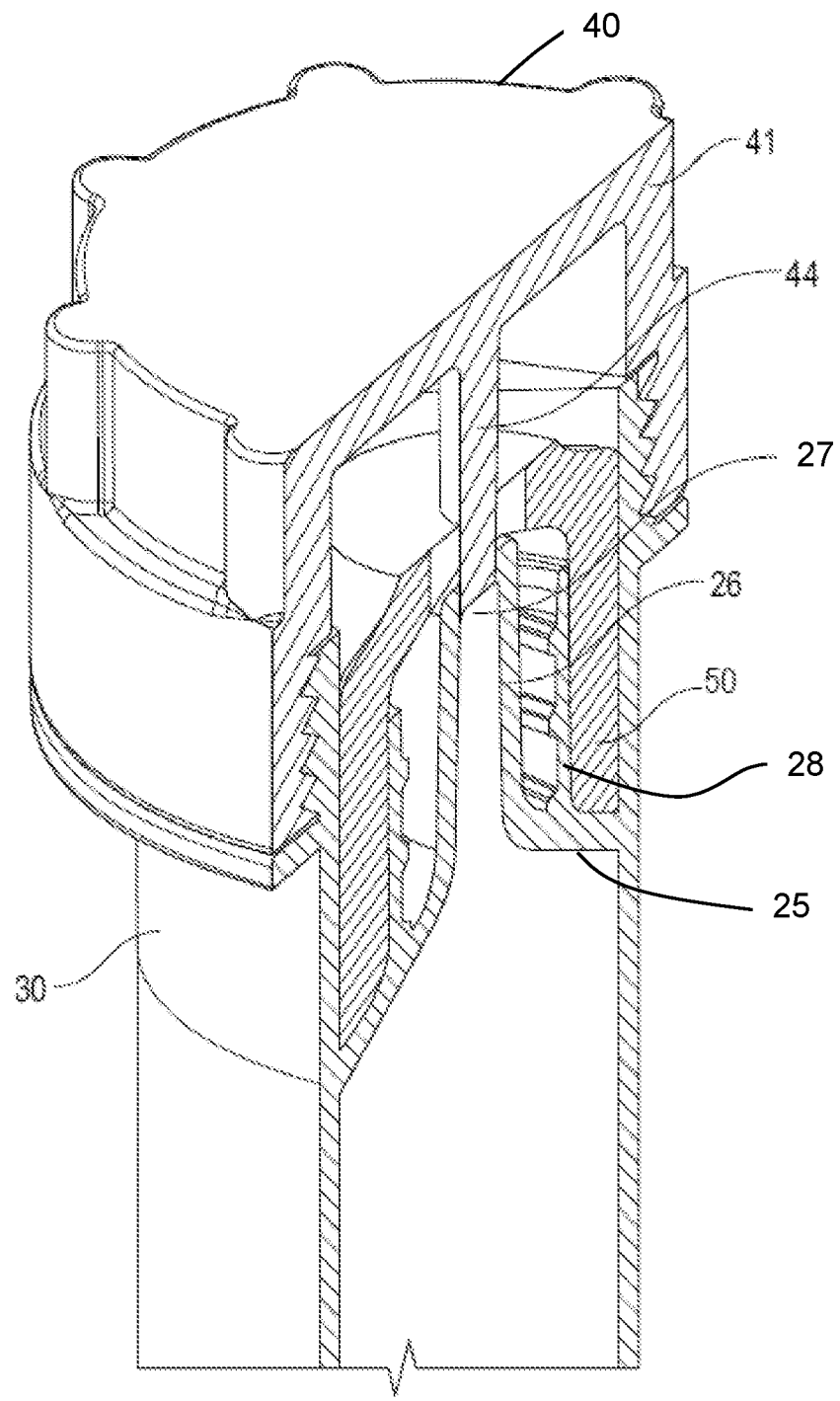
FIG. 20 illustrates a cross-sectional view of a flush syringe with a cap having a protrusion and disinfectant-loaded swab in accordance with one or more embodiments of the present disclosure.

FIG. 17 illustrates a cross-sectional view of a flush syringe with a collar 30 and a cap 40 in accordance with one or more embodiments of the present disclosure. As shown in FIGS. 17 and 20, cap 40 may comprises an outward protrusion 44 that extends from the body 41 of the cap 40 and corresponds with the opening of the distal end of the elongate tip 26. The proximal end 42 of removable cap 40 may comprise a plurality of threads 43 on the inside surface of the cap for attachment to corresponding grooves disposed on the outside surface of the distal end of the collar 30. In one or more embodiments, at least one screw thread adapted to allow the cap to be screwed onto collar 30.

Figure 18:
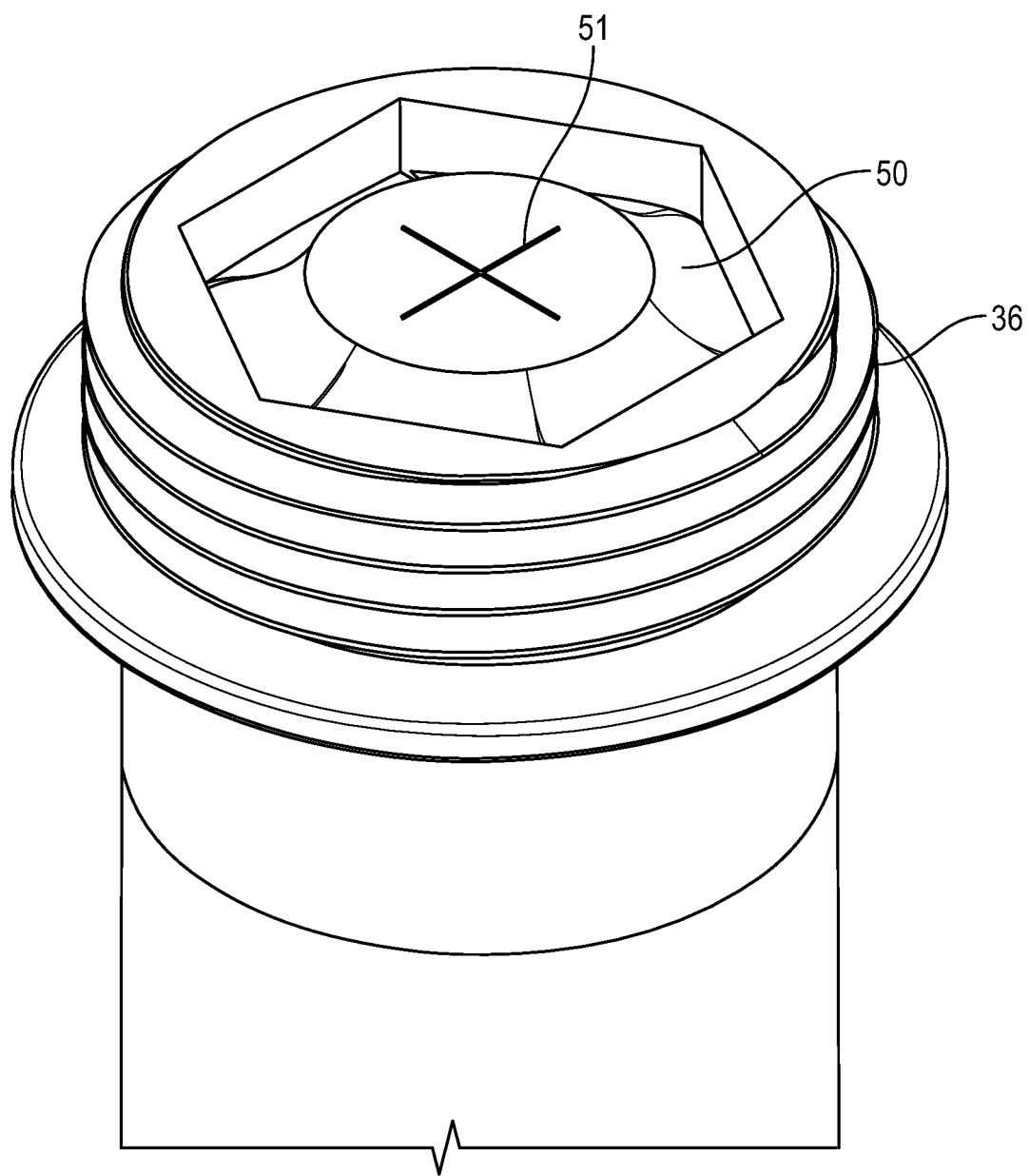
FIG. 18 illustrates a perspective view of a flush syringe with a disinfectant-loaded swab in accordance with one or more embodiments of the present disclosure.
Figure 19:
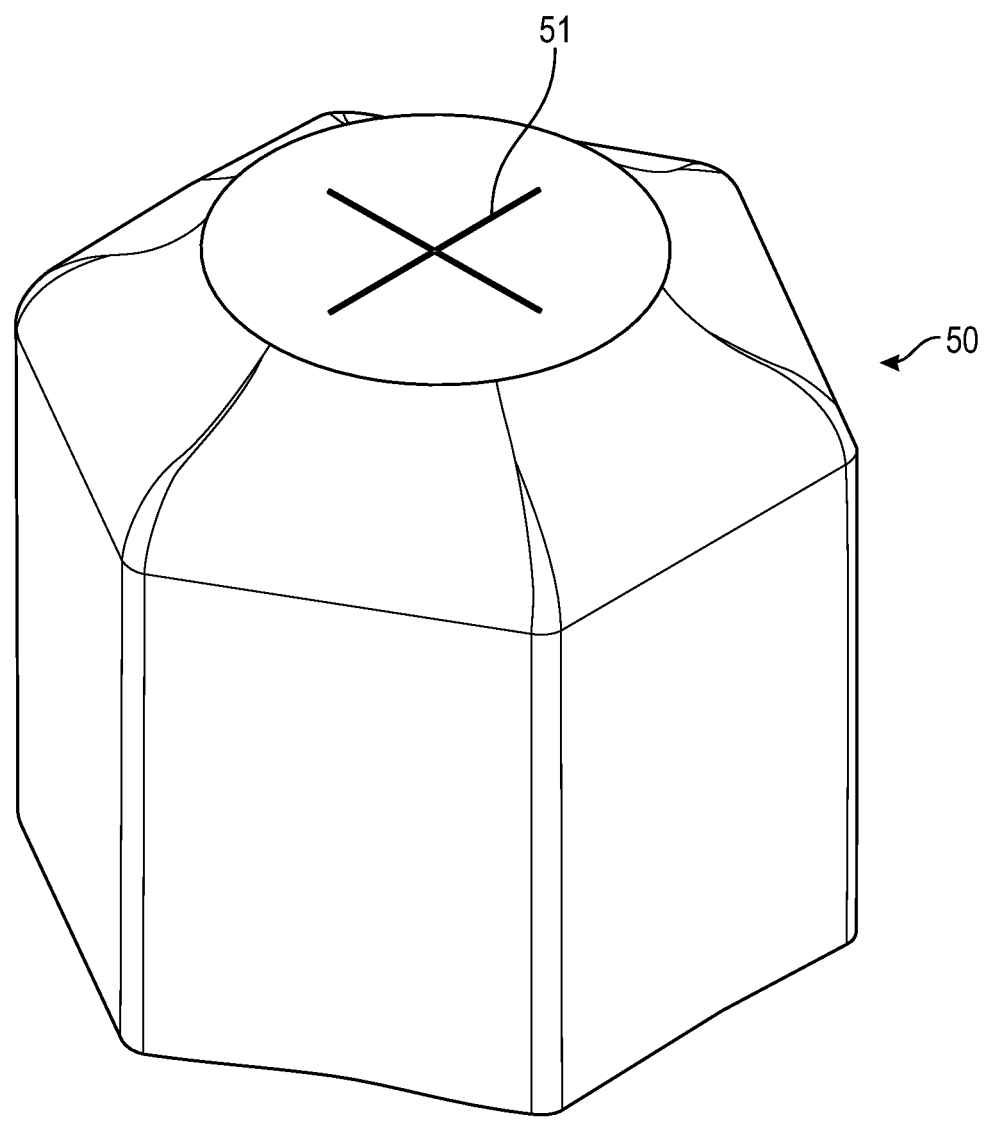
FIG. 19 illustrates a perspective view of a disinfectant-loaded swab in accordance with one or more embodiments of the present disclosure.
Figure 21:
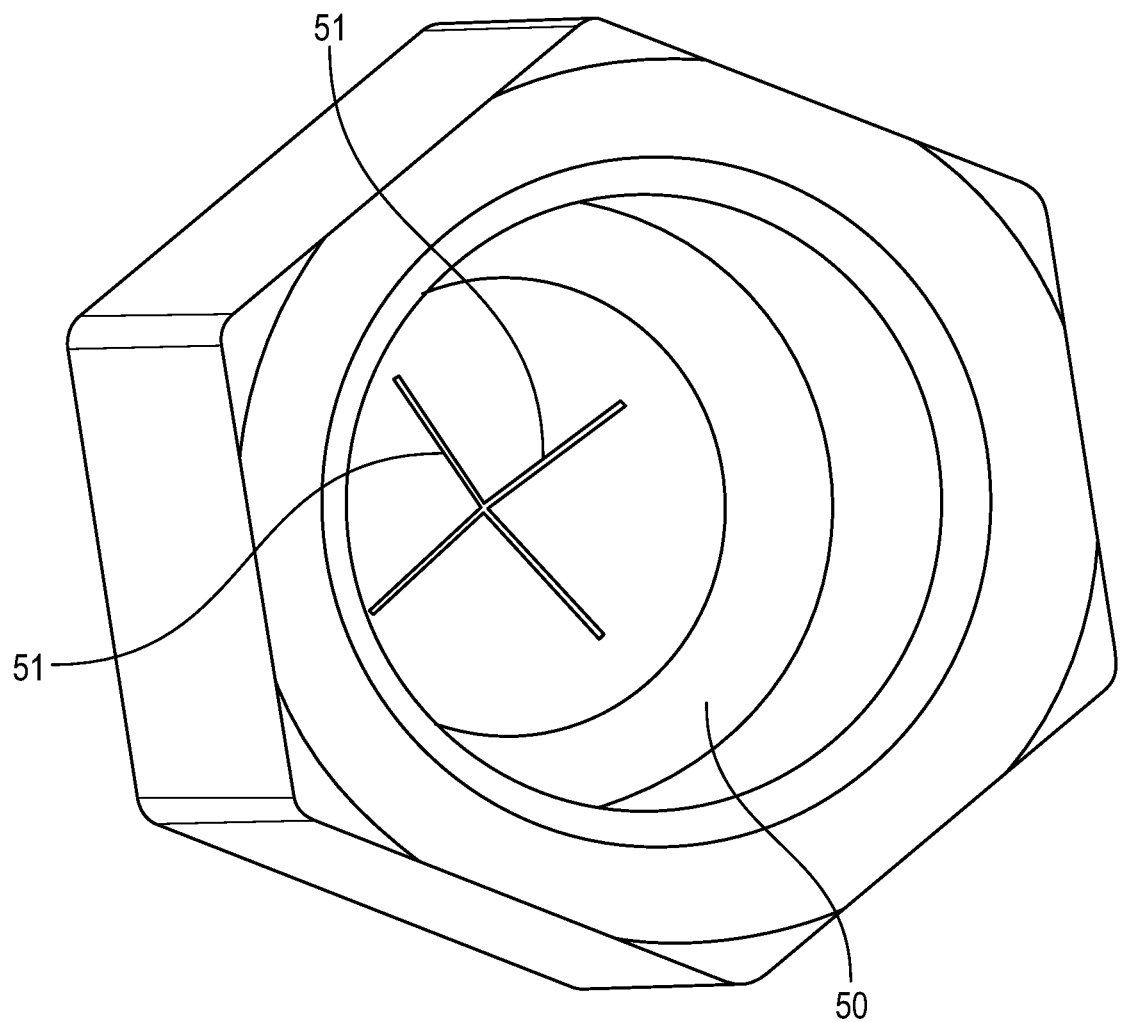
FIG. 21 illustrates a bottom view of a disinfectant-loaded swab in accordance with one or more embodiments of the present disclosure.

As shown in FIGS. 18, 19 and 21, a disinfectant-loaded swab 50 may have a sidewall that is hexagonal in shape that is tapered from the base to the top having a flat top with two slits 51 forming a cross-shaped opening at the top portion of the swab that in accordance with one or more embodiments of the present disclosure.

Figure 22:
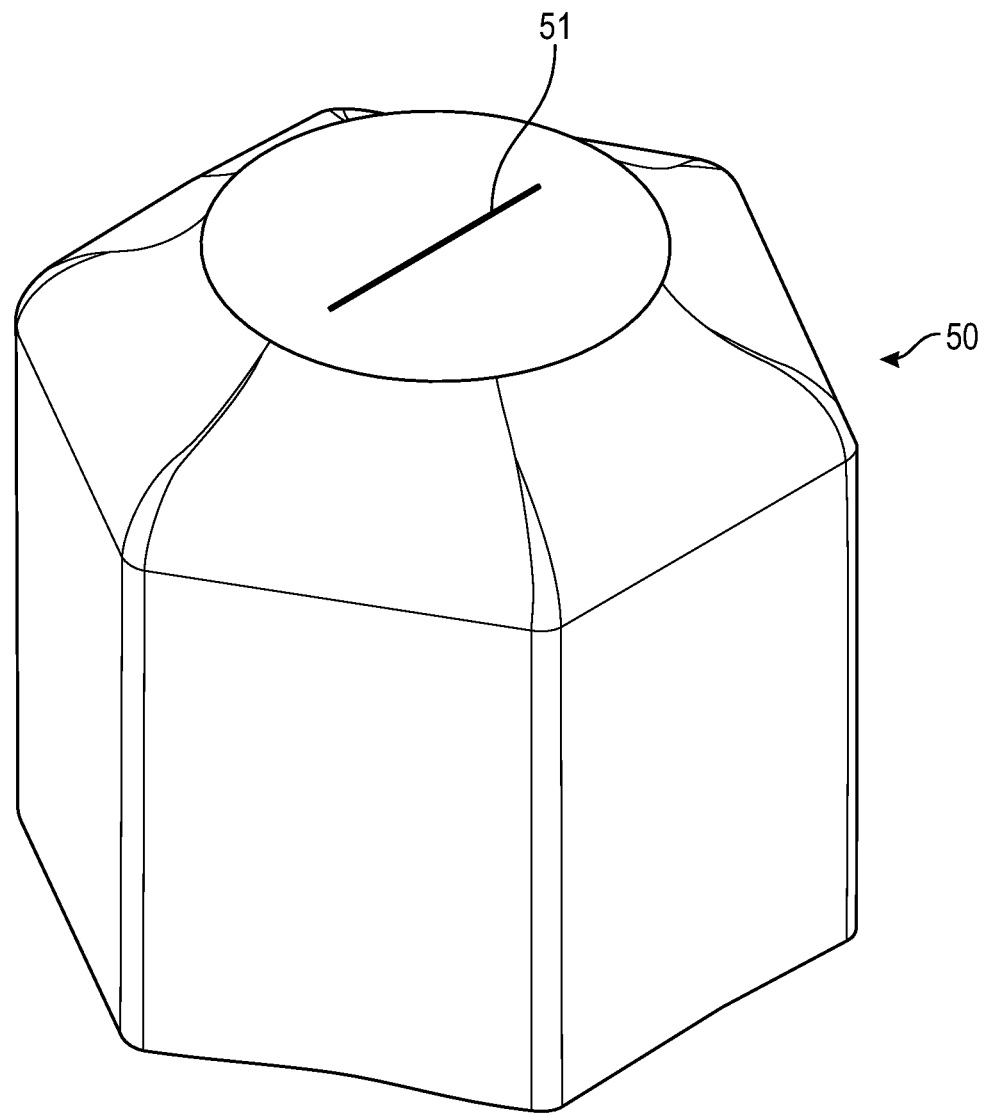
FIG. 22 illustrates a perspective view of a disinfectant-loaded swab having a single slit in accordance with one or more embodiments of the present disclosure.

FIG. 21 illustrates a bottom view of a disinfectant-loaded swab in accordance with one or more embodiments of the present disclosure;

As shown in FIG. 22, a disinfectant-loaded swab 50 may have a sidewall that is hexagonal in shape that is tapered from the base to the top having a flat top with an opening having one slit 51 at the top portion of the swab that in accordance with one or more embodiments of the present disclosure.

Figure 23:
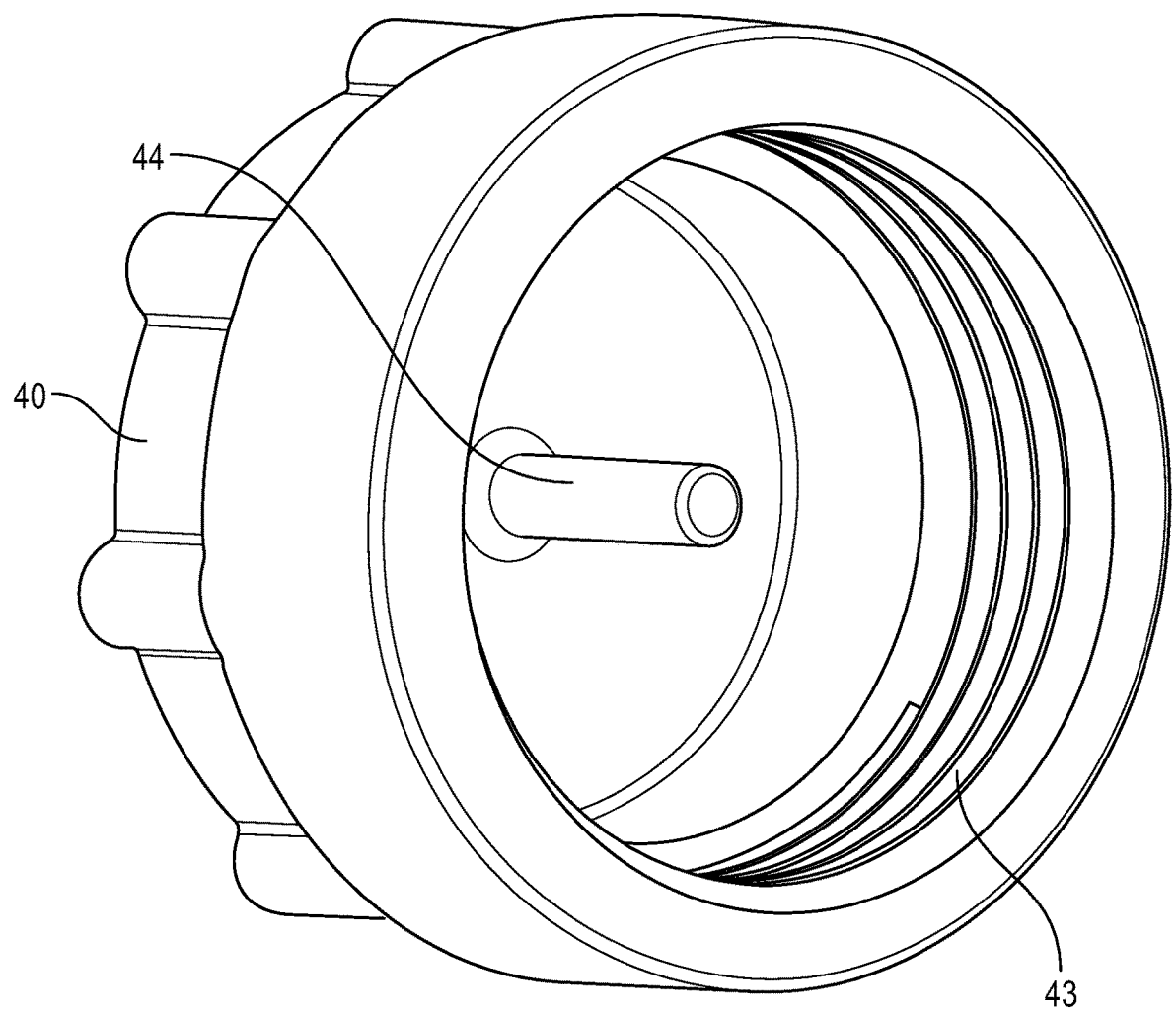
FIG. 23 illustrates a bottom view of a cap having a protrusion in accordance with one or more embodiments of the present disclosure.
Figure 24:
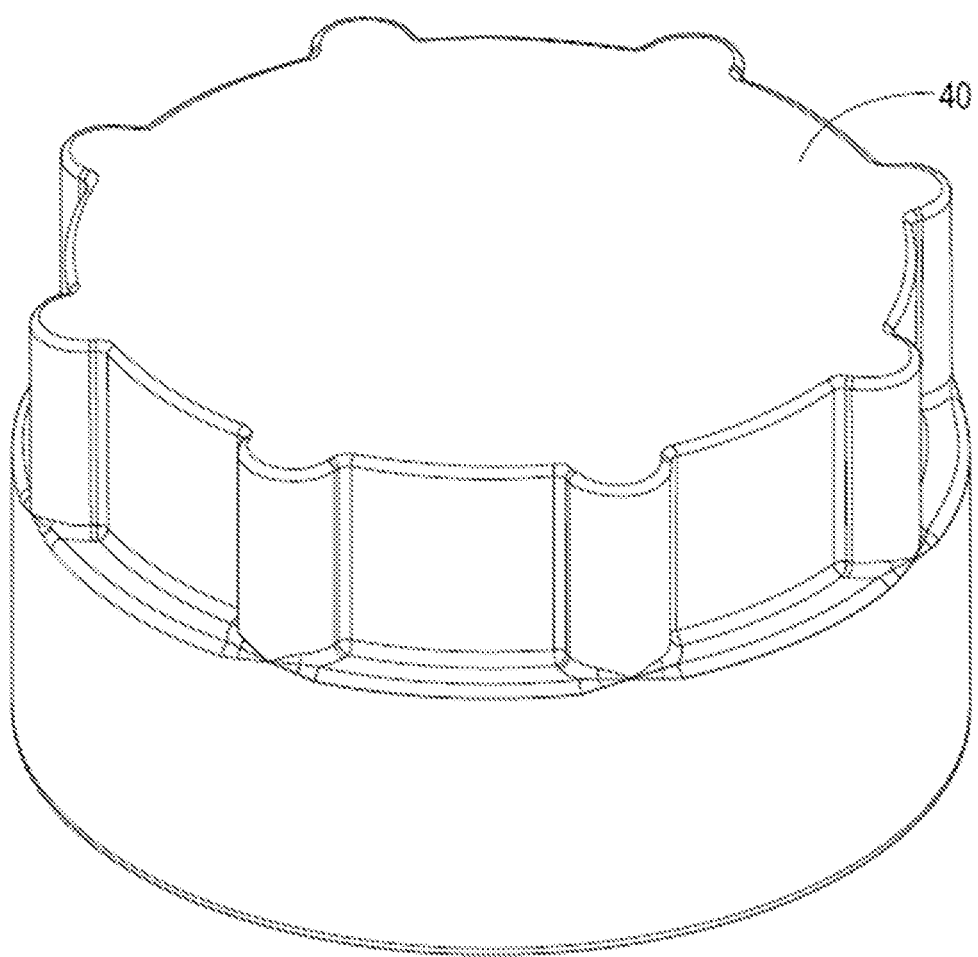
FIG. 24 illustrates a perspective view of a cap in accordance with one or more embodiments of the present disclosure.

As shown in FIGS. 23 and 24, cap 40 may be cylindrical in shape and includes an outward protrusion 44 that extends from the inside surface of the body of the cap 40 and corresponds with the opening of the distal end of the elongate tip 26. The proximal end 42 of removable cap 40 may comprise a plurality of threads 43 on the inside surface of the cap for attachment to corresponding threads 36 disposed on the outside surface of the distal end of the collar 30. In one or more embodiments, at least one screw thread adapted to allow the cap to be screwed onto collar 30.

Figure 25:
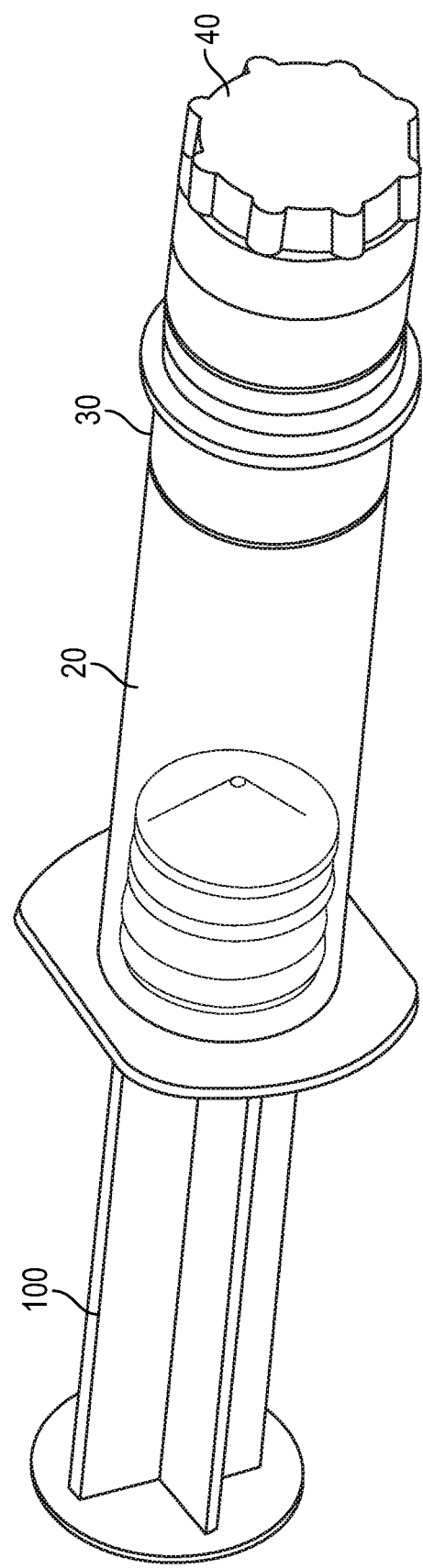
FIG. 25 illustrates a perspective view of a flush syringe with a collar and a cap in accordance with one or more embodiments of the present disclosure.
Figure 26:
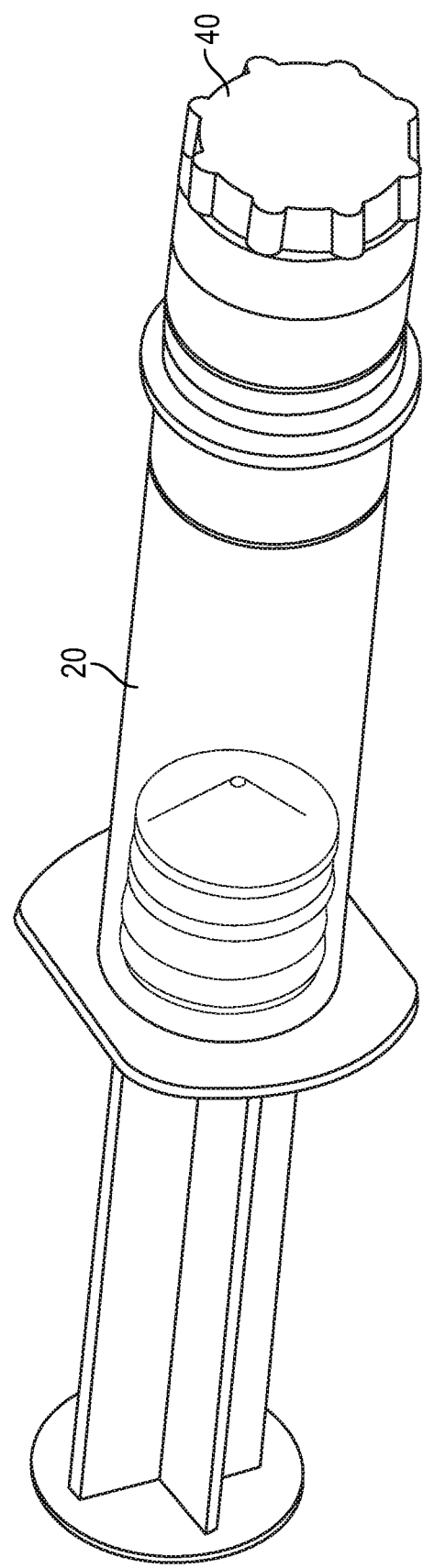
FIG. 26 illustrates a perspective view of a flush syringe with a collar and a cap in accordance with one or more embodiments of the present disclosure.
Figure 27:
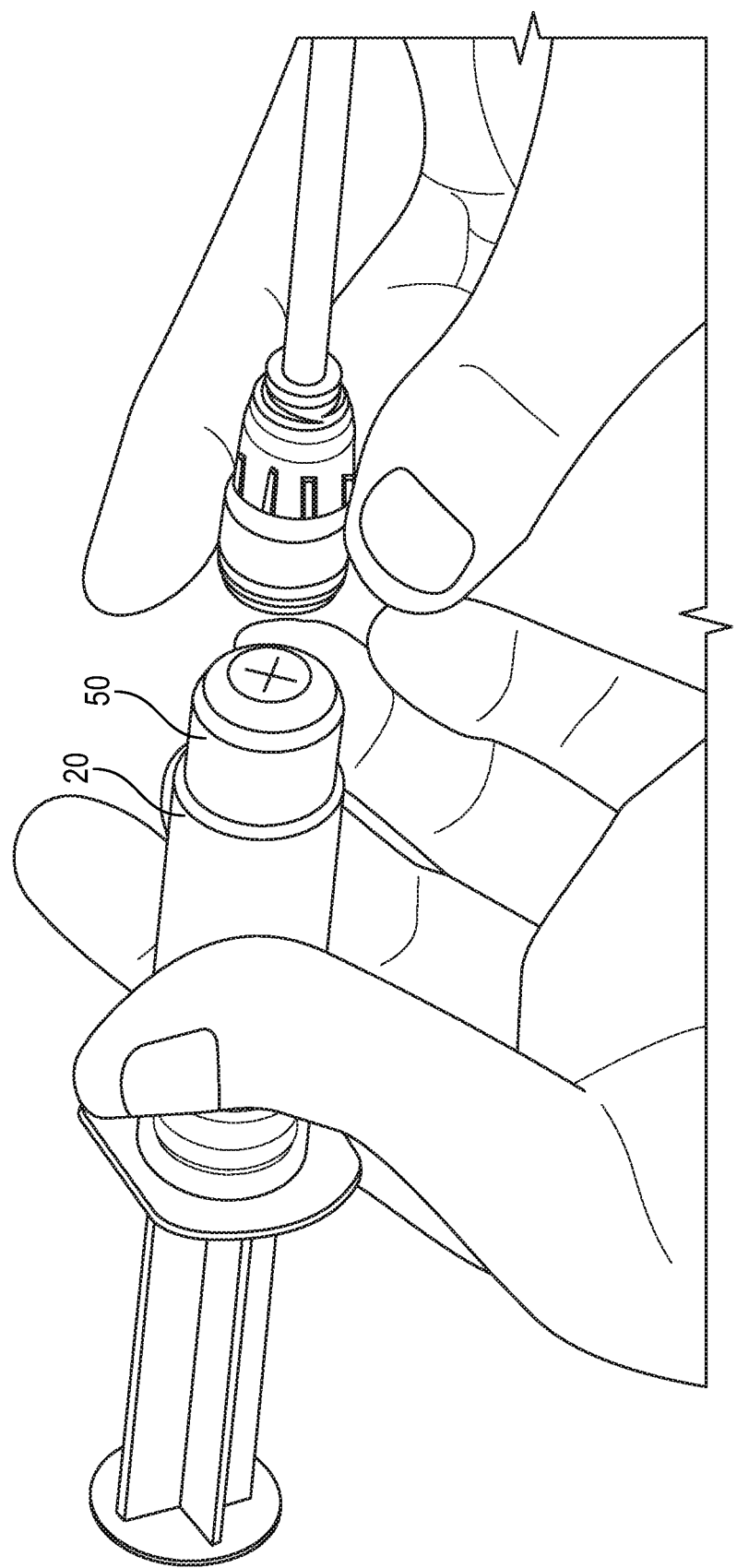
FIG. 27 illustrates a perspective view of a flush syringe with a collar and a swab being attached to a VAD in accordance with one or more embodiments of the present disclosure.
Figure 28:
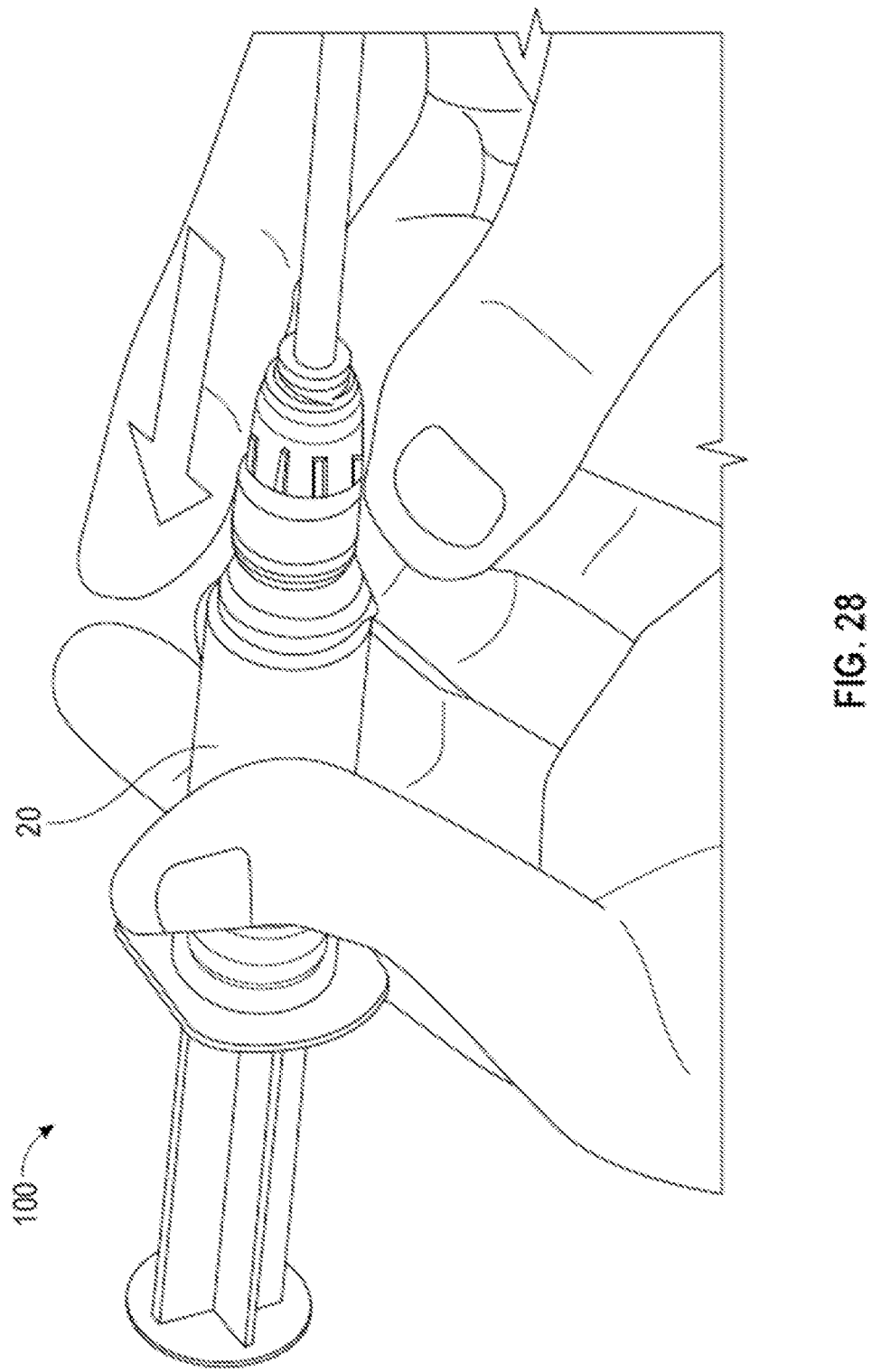
FIG. 28 illustrates a perspective view of a flush syringe with a collar and a swab being attached to a VAD in accordance with one or more embodiments of the present disclosure.
Figure 29:
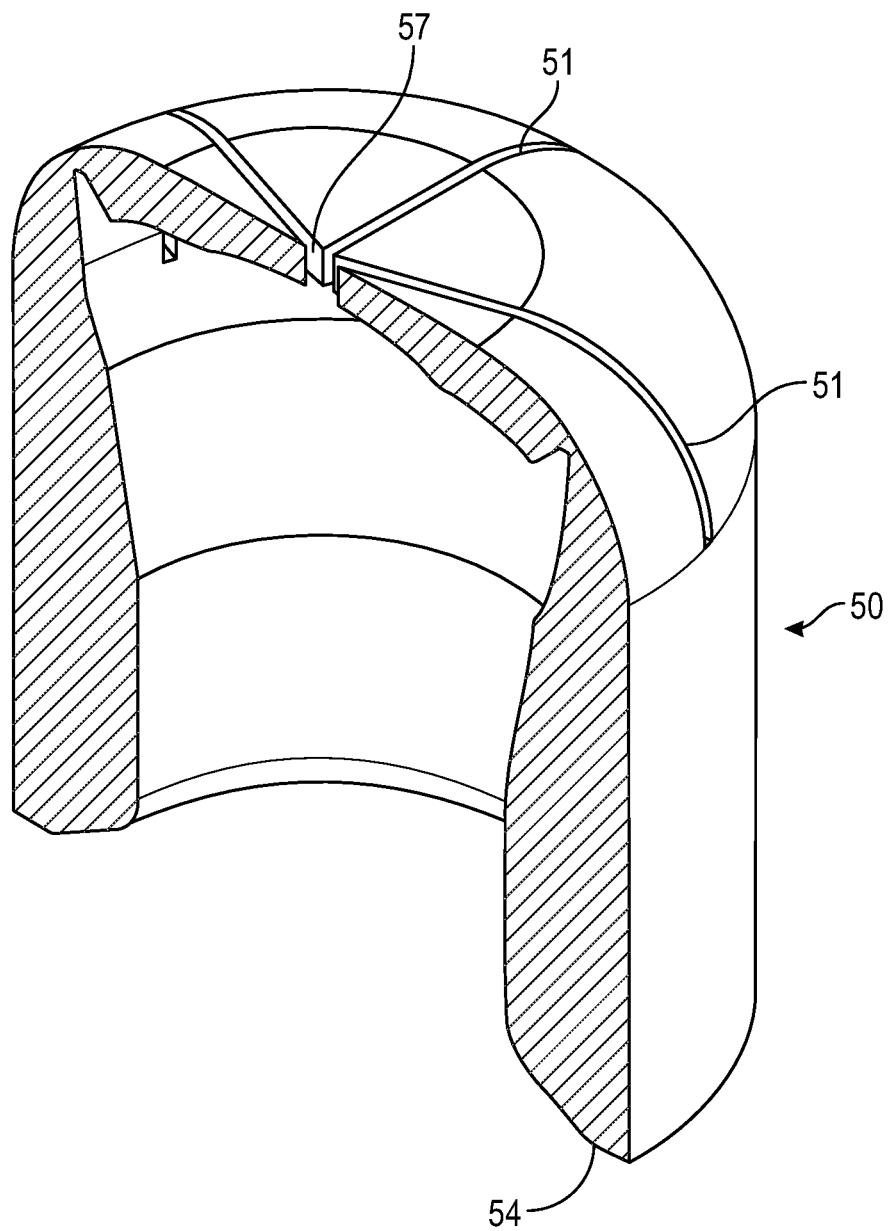
FIG. 29 illustrates a cross sectional view of a swab having multiple slits in accordance with one or more embodiments of the present disclosure.
Figure 30:
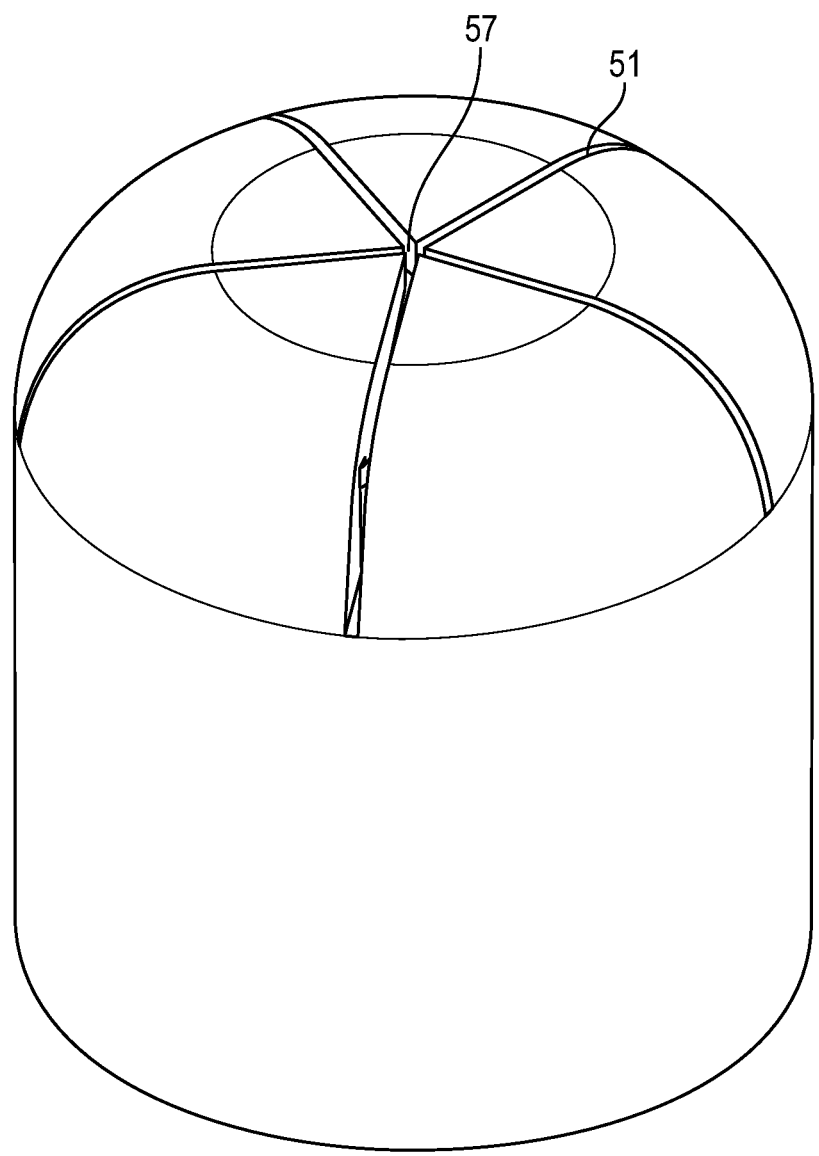
FIG. 30 illustrates a perspective view of a swab as shown in FIG. 29 in accordance with one or more embodiments of the present disclosure.
Figure 31:
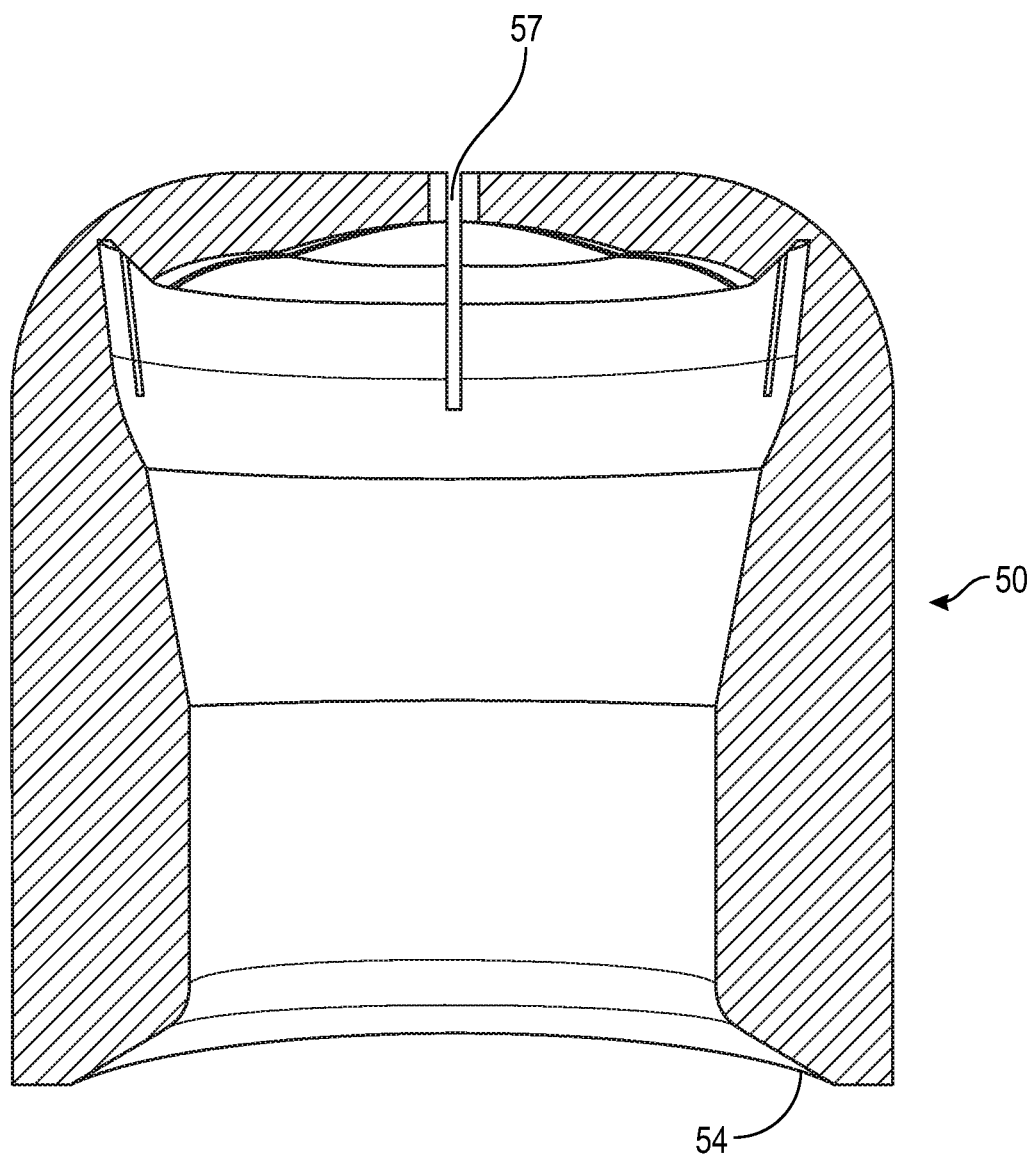
FIG. 31 illustrates a cross-sectional side view of a swab as shown in FIG. 29 in accordance with one or more embodiments of the present disclosure.
Figure 32:
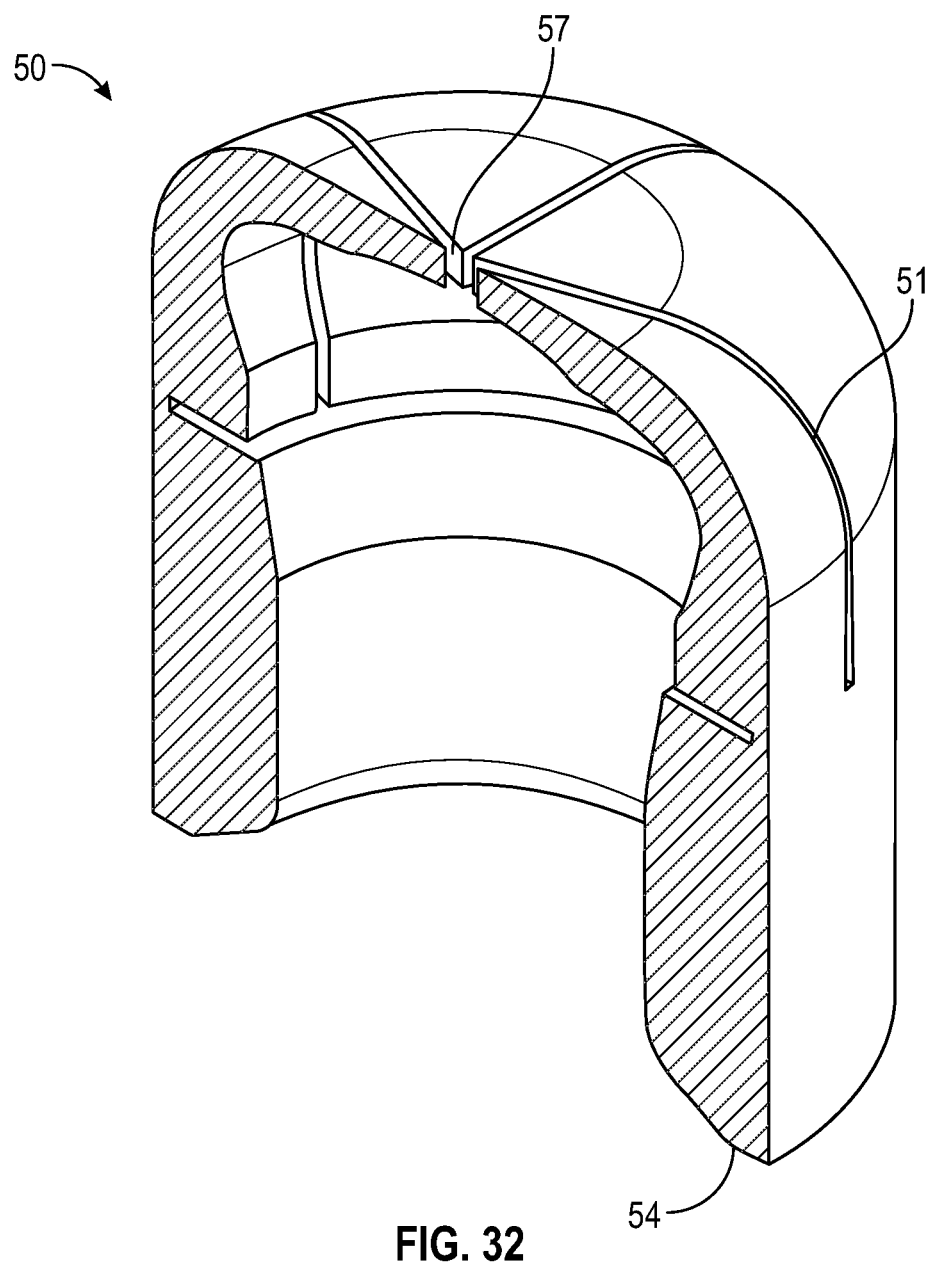
FIG. 32 illustrates a cross-sectional view of a swab as shown in FIG. 29 in accordance with one or more embodiments of the present disclosure.
Figure 33:
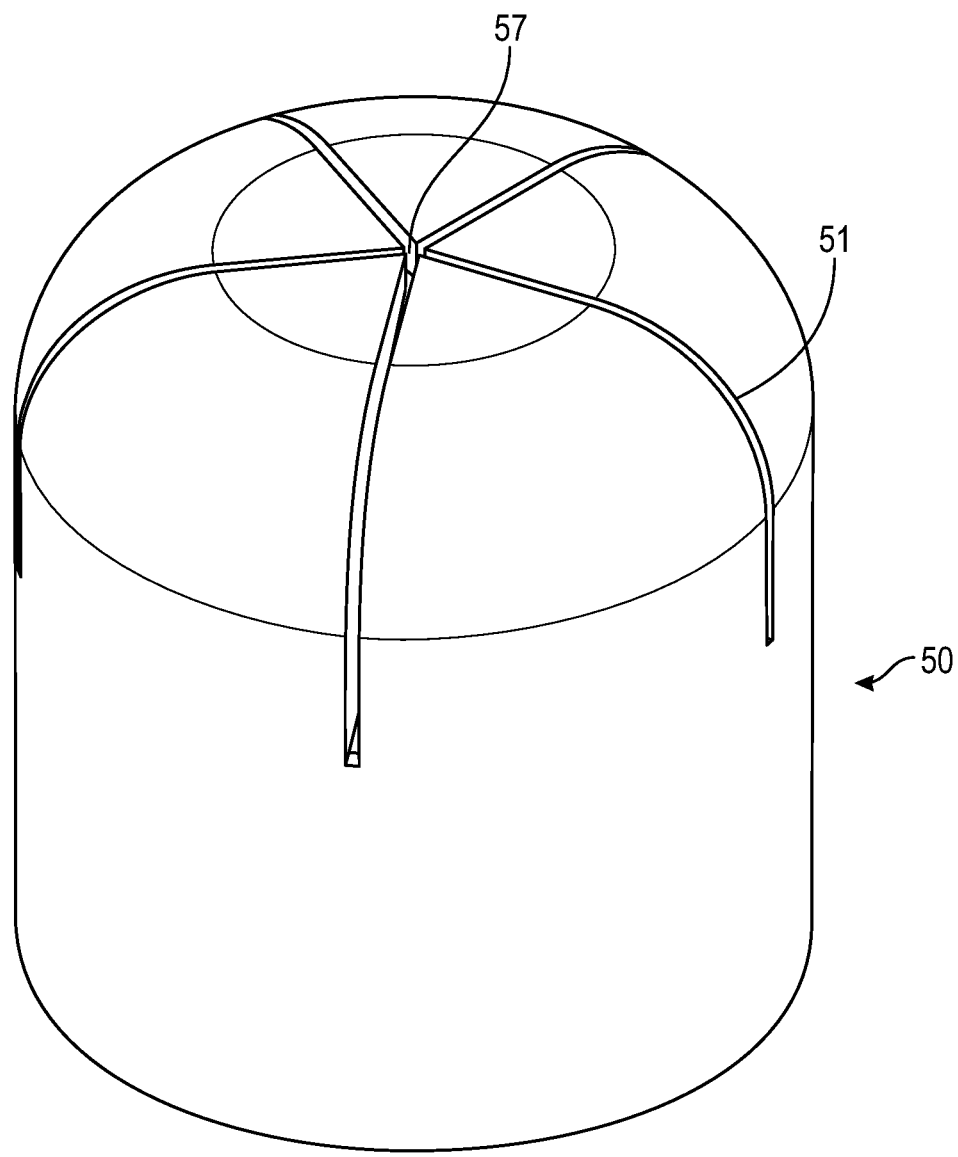
FIG. 33 illustrates a perspective view of a swab in accordance with one or more embodiments of the present disclosure.
Figure 34:
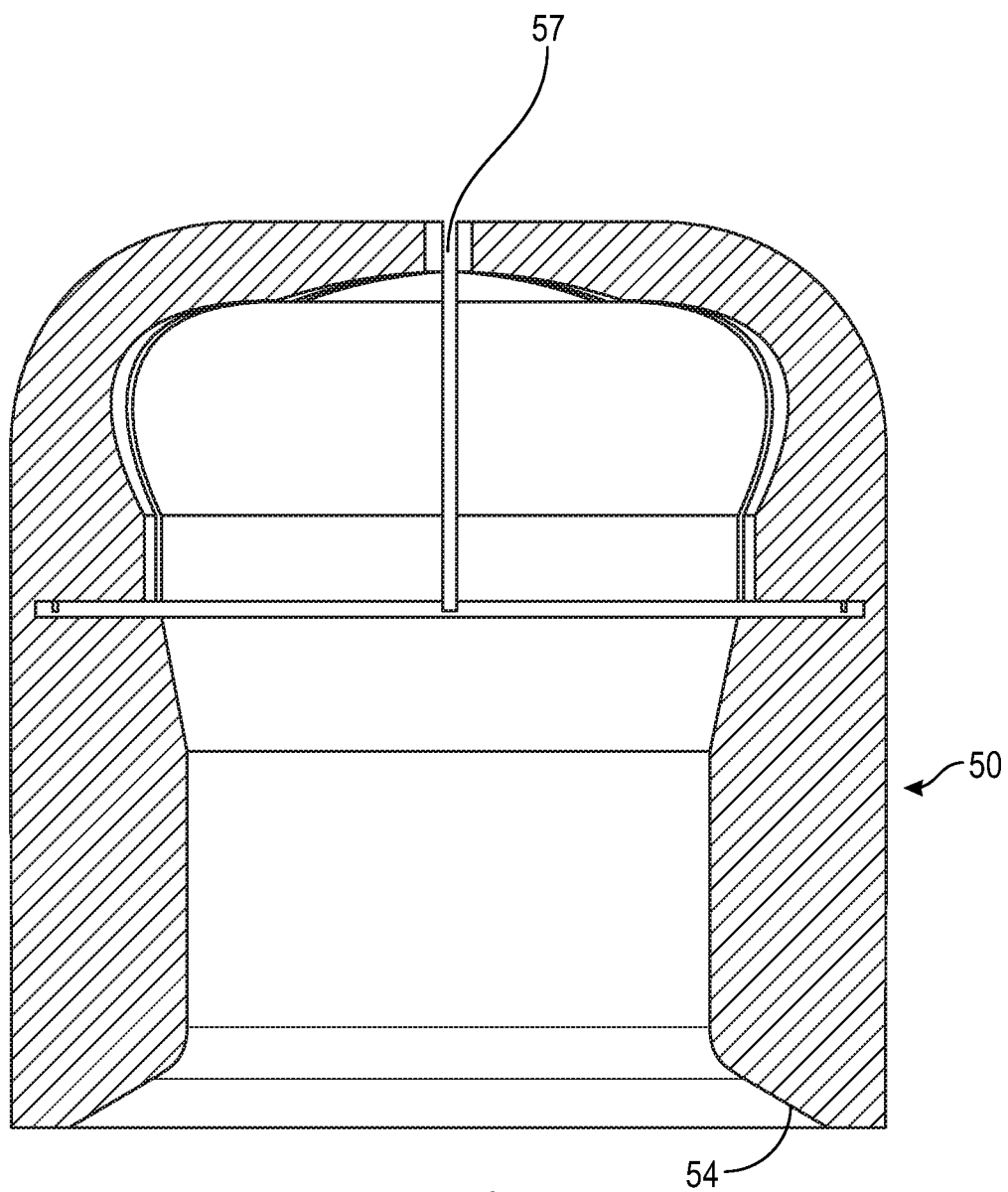
FIG. 34 illustrates a cross-sectional side view of a swab in accordance with one or more embodiments of the present disclosure.
Figure 35:
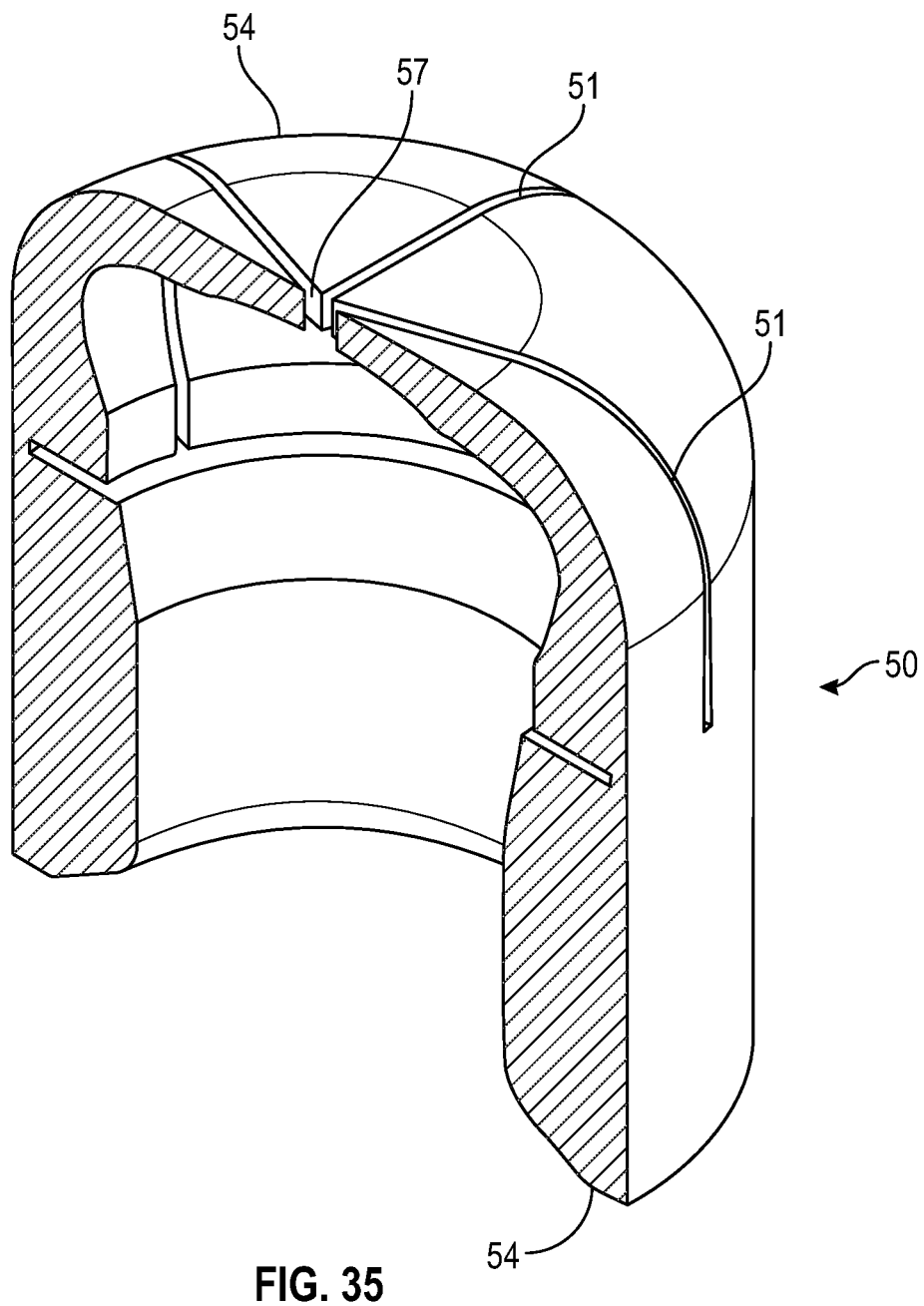
FIG. 35 illustrates a cross-sectional view of an alternate swab in accordance with one or more embodiments of the present disclosure.
Figure 36:
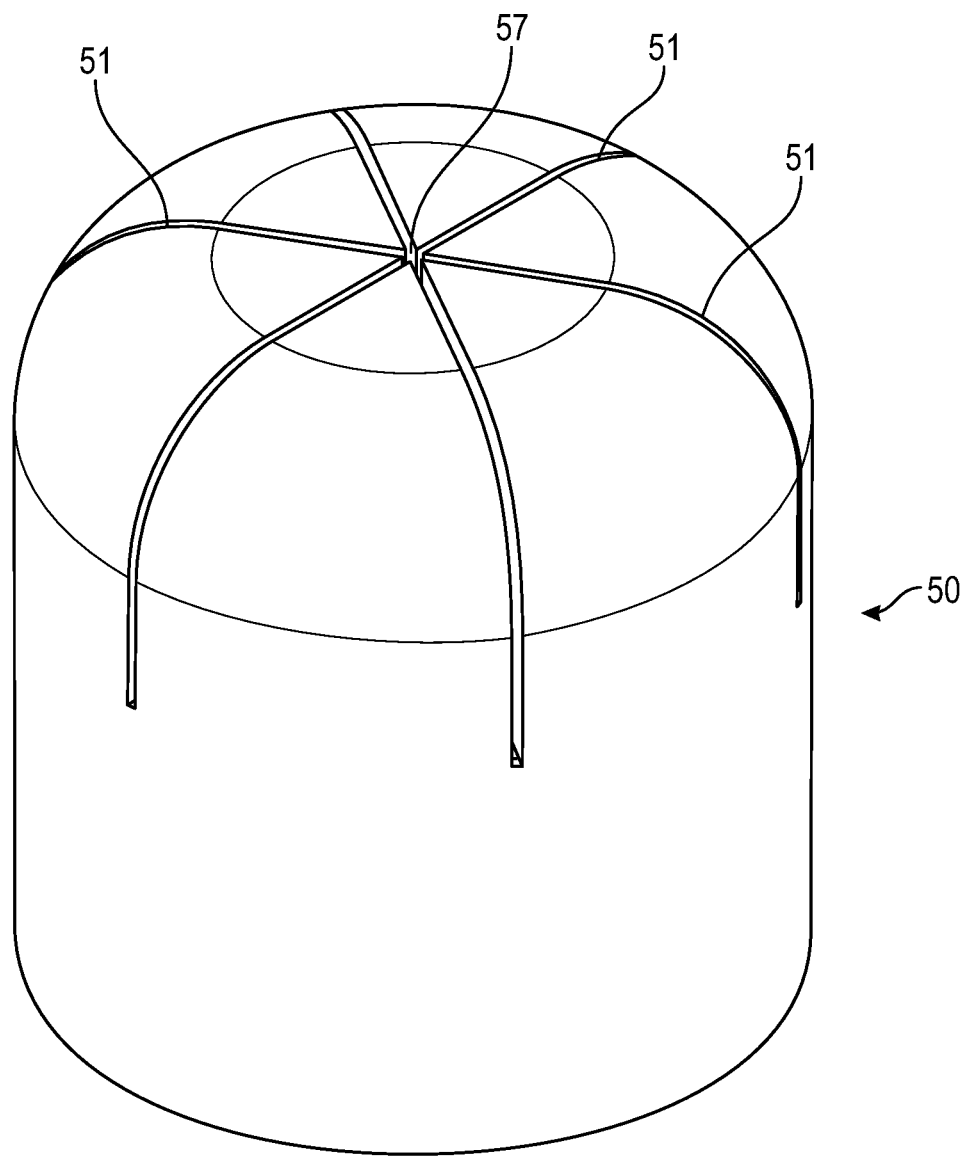
FIG. 36 illustrates a perspective view of a swab as shown in FIG. 35 in accordance with one or more embodiments of the present disclosure.
Figure 37:
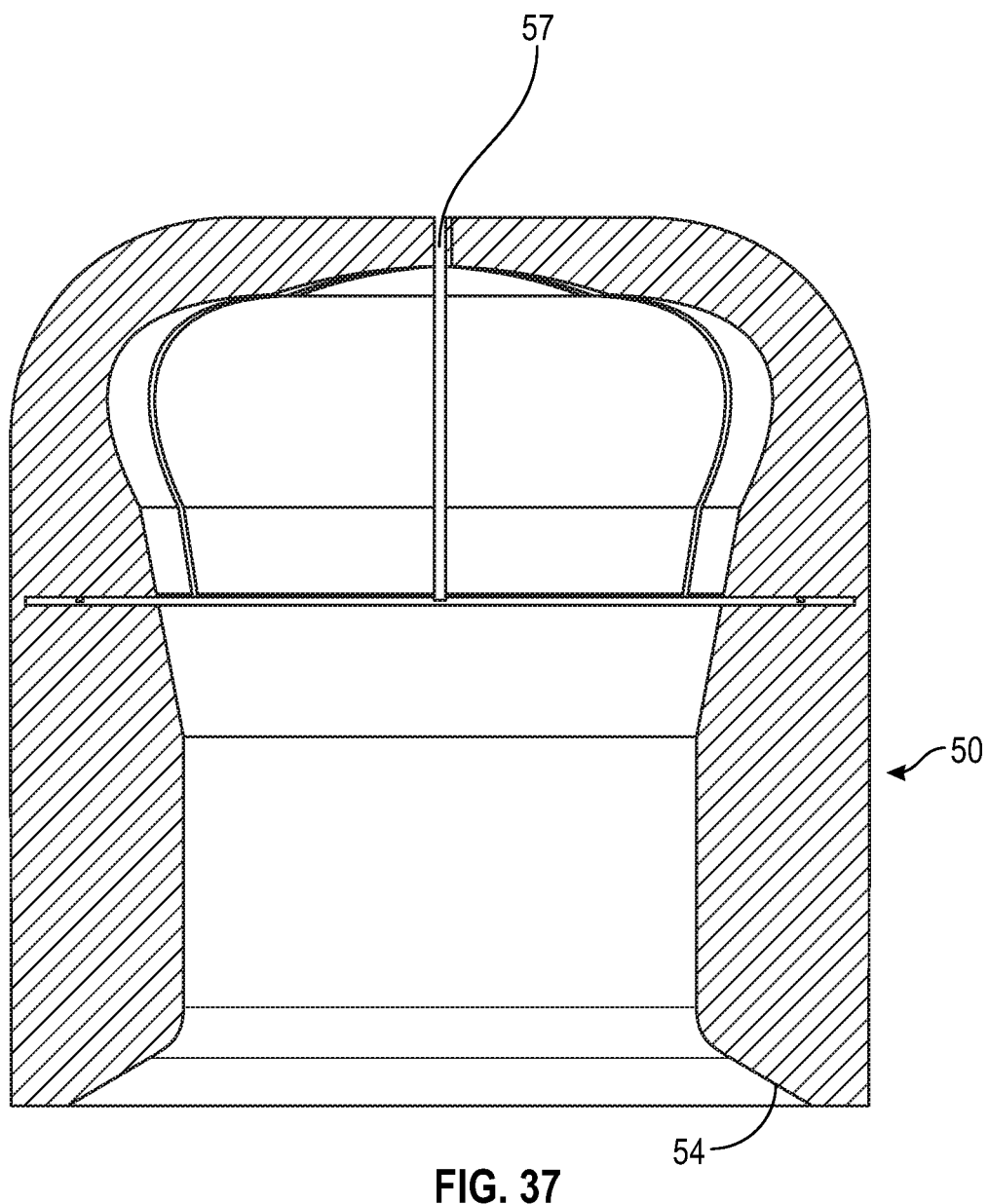
FIG. 37 illustrates a cross sectional side view of a swab as shown in FIG. 35 in accordance with one or more embodiments of the present disclosure.

FIGS. 25 and 26 illustrates a syringe assembly having a cap 40 covering the swab 50 prior to connection of the syringe assembly with a corresponding medical connector or VAD in accordance with one or more embodiments of the present disclosure. FIG. 27 show the flush syringe with cap removed prior to connection with a corresponding medical connector or VAD and FIGS. 27 and 28 illustrates a flush syringe with a collar and a swab being attached to a VAD in accordance with one or more embodiments of the present disclosure.

As shown in FIGS. 29-37, an alternate embodiment of a frusto-conical or dome shaped swab of the present disclosure includes a tapered sidewall wherein the thickness of the sidewall 54 decreases from the base of the swab towards the top of the swab. The radius at the opening of the cavity of the swab toward the base of the swab is smaller than the radius of the cavity towards the top of the cavity of the swab. As shown in FIGS. 29-32, the swab includes multiple slits 51 that converge to form a center opening 57.

Figure 38:
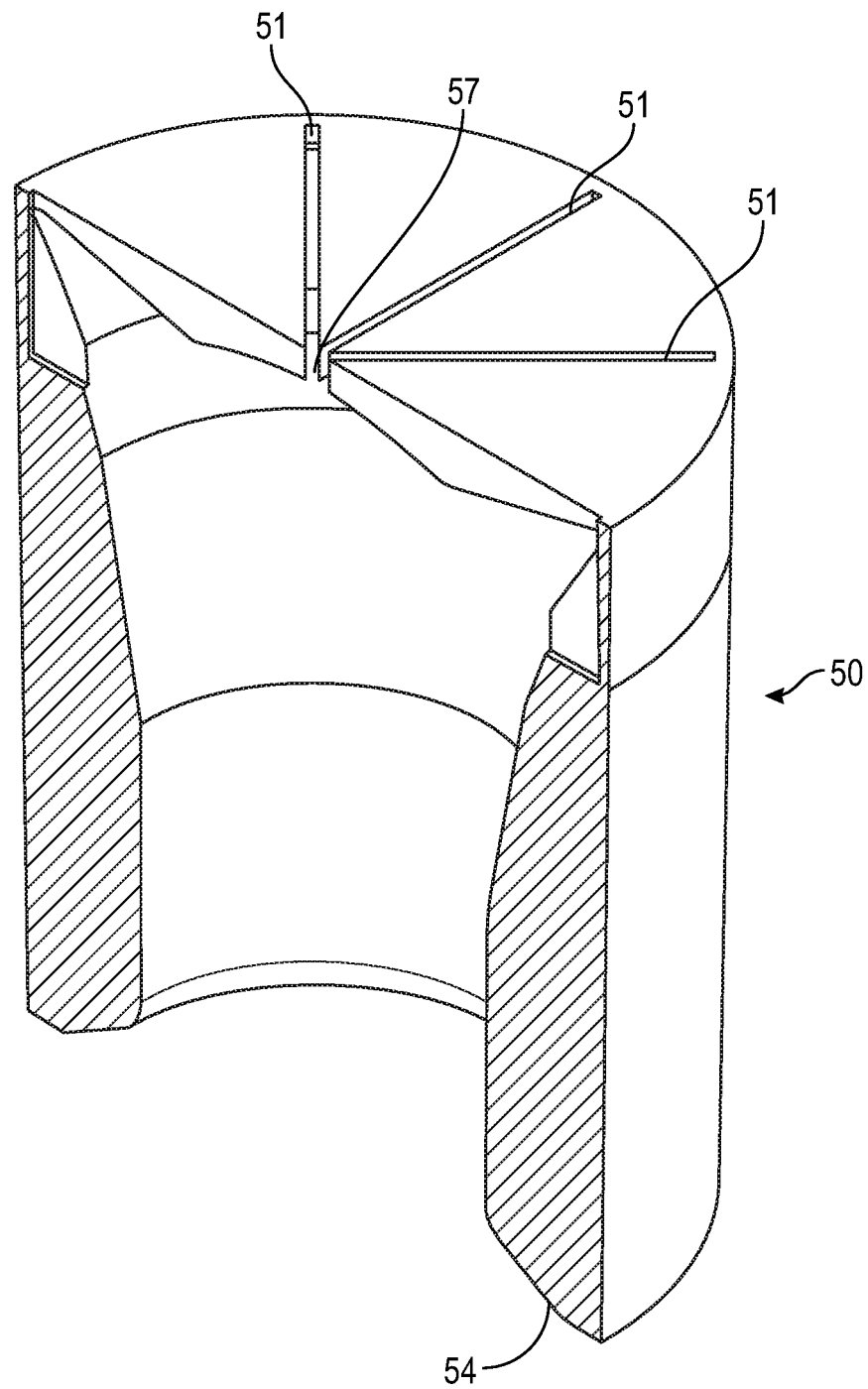
FIG. 38 illustrates a cross sectional view of an alternate swab in accordance with one or more embodiments of the present disclosure.
Figure 39:
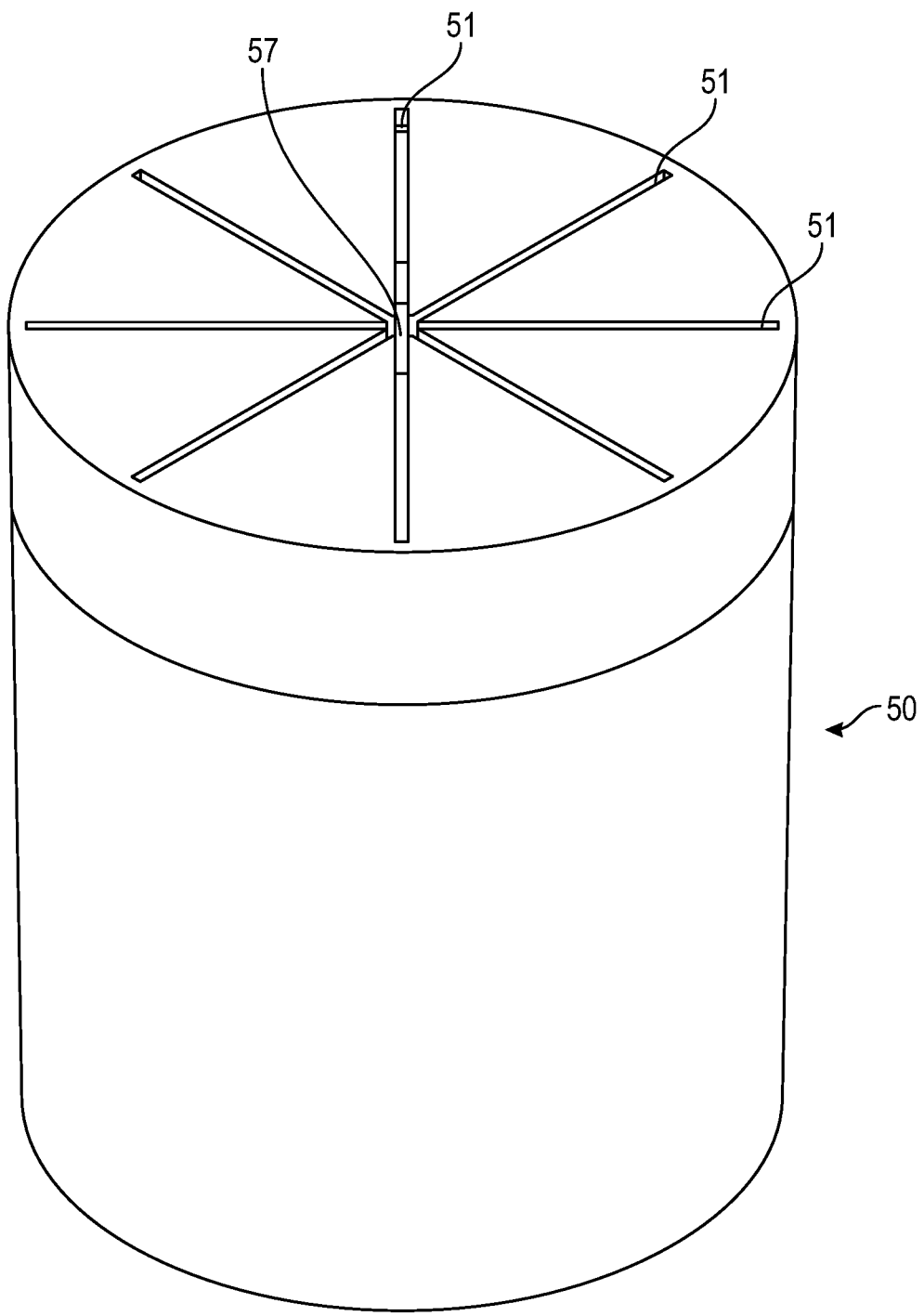
FIG. 39 illustrates a perspective view of a swab as shown in FIG. 38 in accordance with one or more embodiments of the present disclosure.
Figure 40:
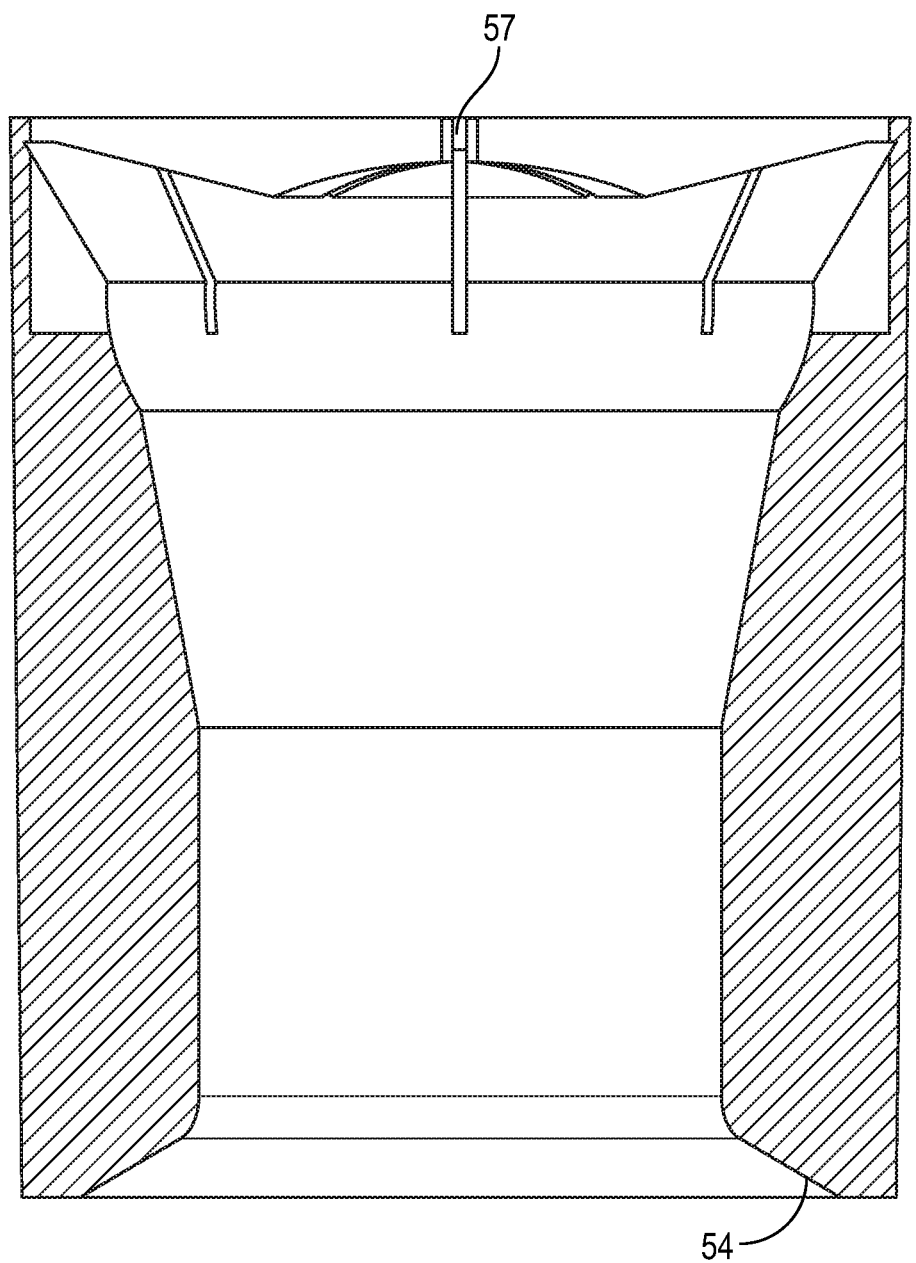
FIG. 40 illustrates a cross-sectional side view of a swab as shown in FIG. 38 in accordance with one or more embodiments of the present disclosure.

As shown in FIGS. 38-40, an alternate embodiment of a cylindrical shaped swab of the present disclosure includes a tapered sidewall wherein the thickness of the sidewall 54 decreases from the base of the swab towards the top of the swab. The radius at the opening of the cavity of the swab toward the base of the swab is smaller than the radius of the cavity towards the top of the cavity of the swab. As shown in FIGS. 38-40, the swab includes multiple slits 51 that converge to form a center opening 57.

Figure 41:
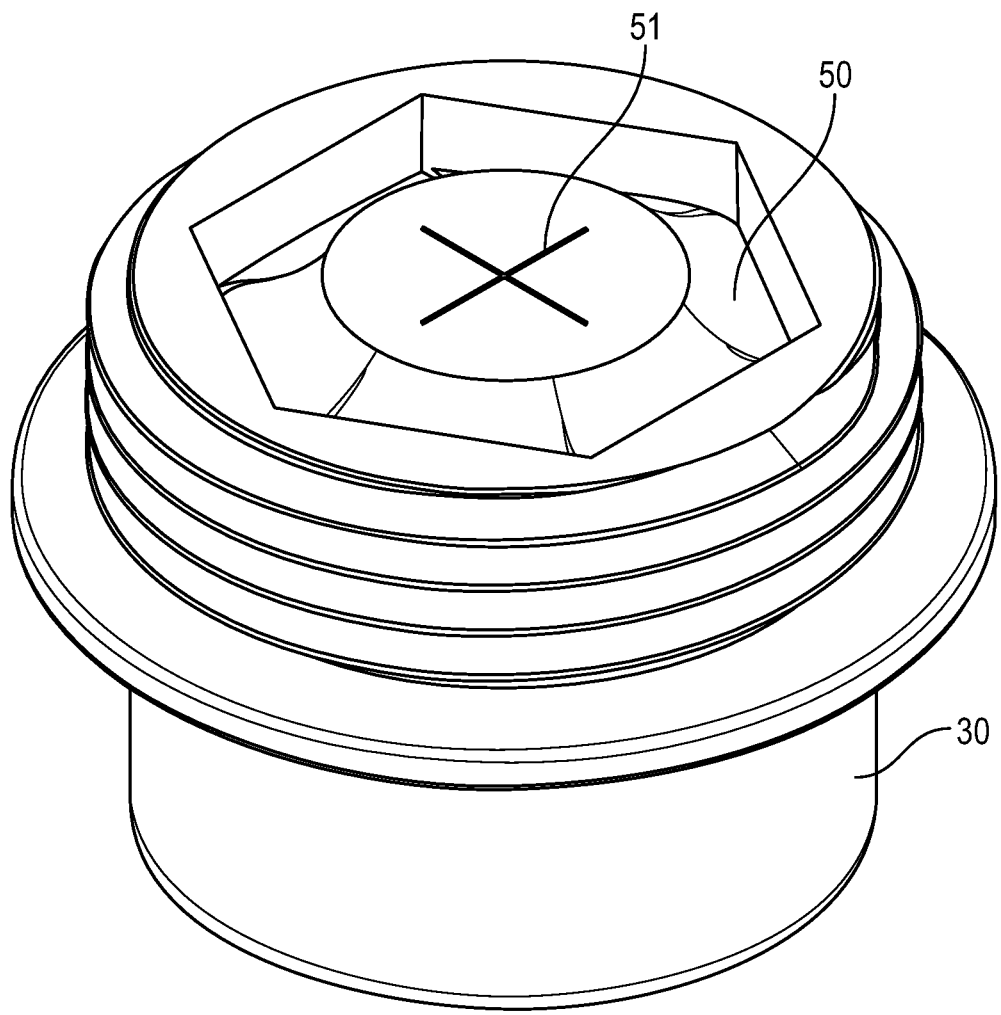
FIG. 41 illustrates a top perspective view of a collar and swab in accordance with one or more embodiments of the present disclosure.
Figure 42:
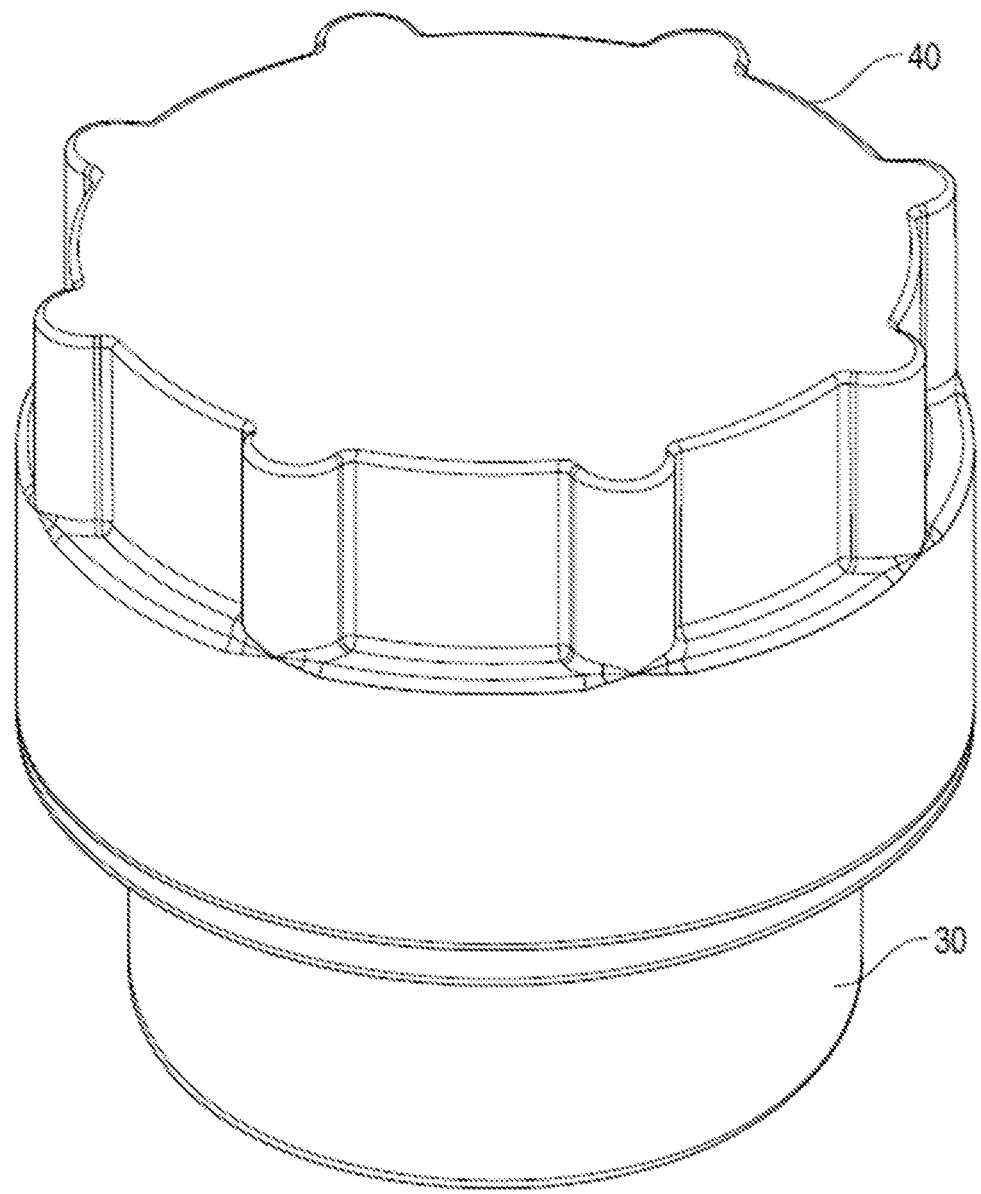
FIG. 42 illustrates a perspective view of a collar and cap in accordance with one or more embodiments of the present disclosure.
Figure 44:
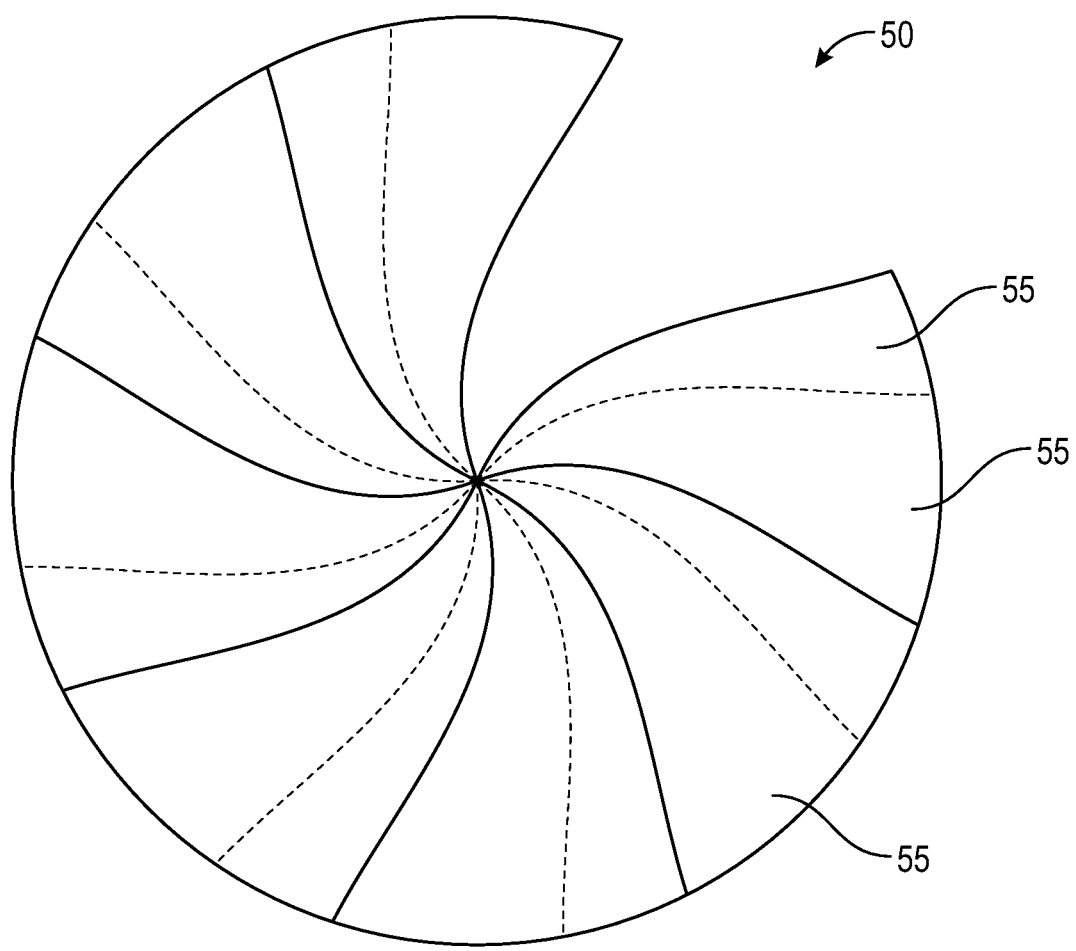
FIG. 44 illustrates a perspective view of a flush syringe with overlapping flaps in accordance with one or more embodiments of the present disclosure.

Disinfectant-loaded swab 50 can have a near cylindrical or hexagonal outer surface, as seen in FIGS. 41 and 42. The purpose of the hexagonal shape combined with the barrel 20 with the collar 30 is to provide a strong grip between the collar 30 and disinfectant-loaded swab 50 and prevent disinfectant-loaded swab 50 from rotating as the syringe assembly 10 gets twisted onto a VAD connector. The inner surface of the collar 30 can be cylindrical or hexagonal or any other geometry to increase friction between the disinfectant-loaded swab 50 and barrel 20. The opening at the top of the disinfectant-loaded swab 50 can be a single slit, two or more slits. Alternatively, as seen in FIG. 44, the top surface disinfectant-loaded swab 50 can be with a number of overlapping flaps 55 at the top surface. A portion of each flap 55 overlaps with the next and so on. Overlapping flaps 55 on the top of the swab 50 are positioned to open in the direction of twisting of the cap onto a corresponding connector. In one or more embodiments, the thickness of disinfectant-loaded swab 50 can be adjusted to enable absorbance of sufficient amounts of disinfectant. Further, the inner surface of the disinfectant-loaded swab 50 may have various forms of cut-outs to allow for the disinfectant-loaded swab 50 to buckle and fold on itself and allow the penetration of needleless connector. In one or more embodiments, as shown in FIGS. 29-40, there is some open space inside of the swab to create space for the pieces of the swab that enter that space as the disinfectant-loaded swab 50 opens. In an alternate embodiment, the disinfectant-loaded swab 50 fully rolls up on the sides of the needleless connector like a sleeve. The porosity of the disinfectant-loaded swab 50 can be different throughout the disinfectant-loaded swab 50 (e.g. a radial or axial gradient or else) to allow for controlling the absorbance and release of the disinfectant. Additionally, the top surface can bear additional surface features for improving the scrubbing. A range of disinfectants (e.g. IPA, ethanol, chlorhexidine, etc.) at various concentrations can be loaded into the swab.

In one or more embodiments of the present disclosure, the disinfectant-loaded swab 50 can sit on top of the syringe tip without lateral support. In such embodiments, a tip cap 40 can be threaded onto the distal end of the barrel near the swab. The distal end of the barrel will have one or more plurality of threads. In one or more embodiments, the distal end 34 of the collar 30 may comprise a removable seal 60. The removable seal 60 can comprise an aluminum peal back top. The seal can be a plastic sealed aluminum, and can be chemically-resistant, light-blocking, non-permeable, or sterile.

In one or more embodiments, the collar 30 may also comprise an aluminum lining adhered to the inside surface of at least one side wall 31. The aluminum lining can prevent degradation of the disinfectant or antimicrobial agent, and can also provide a mechanism for ensuring compliance with aseptic conditions.

As shown in FIG. 1, the open distal end 34 of the collar 30 may comprise a removable cap 40. The removable cap 40 includes a body with a proximal end 42, a closed distal end 43. The distal end 43 and the proximal end 42 define the length of the cap 40. Upon assembly, the proximal end 42 of the cap 40 is adjacent the distal end 34 of the collar 30.

The cross-sectional shape of the cap 40 can be any suitable shape including, but not limited to, triangular, square, pentagonal, hexagonal, heptagonal, octagonal, symmetric or non-symmetric polygonal. The shape of the cap 40 can provide a comfortable feel for the user and enhanced gripping ability to allow the user to easily connect or disconnect the cap from the collar 30.

The syringe assembly 10 having collar 30 and disinfectant-loaded swab 50 including an absorbent material surrounding tip 26 that is rendered antimicrobial because the tip is surrounded by an absorbent material that soaks up disinfectant or antimicrobial agent contained within compartment 33. The now antimicrobial tip 26 can be connected to a vascular access device. In necessary, cap 40 or seal 48 is removed from the distal end 34 of the collar 30, exposing the tip 26. As the syringe assembly 10 is connected to the hub of a vascular access device 60, the disinfectant-loaded swab 50 compresses creating friction. The disinfecting properties of the disinfectant or antimicrobial agent contained within the disinfectant-loaded swab 50 disposed in compartment 33 that has been absorbed by absorbent material, disinfect the hub 60 of a vascular access device, thus ensuring compliance with aseptic technique. The friction created by the compression of the disinfectant-loaded swab 50 is necessary to provide disinfection of the hub 60. Once the connection of the syringe assembly 10 to the hub 60 is completed, the hub is properly disinfected, and fluid communication from the barrel 20 of the syringe to the vascular access device can occur. Fluid is drawn from the barrel 20 through the passageway 27 through the hub 60 and into the IV or catheter. Because of the presence of the collar 30 and disinfectant-loaded swab 50, fluid communication through a vascular access device and into a patient is conducted under aseptic conditions without any additional swabbing steps and diligence on the part of the clinician.

Figure 43:
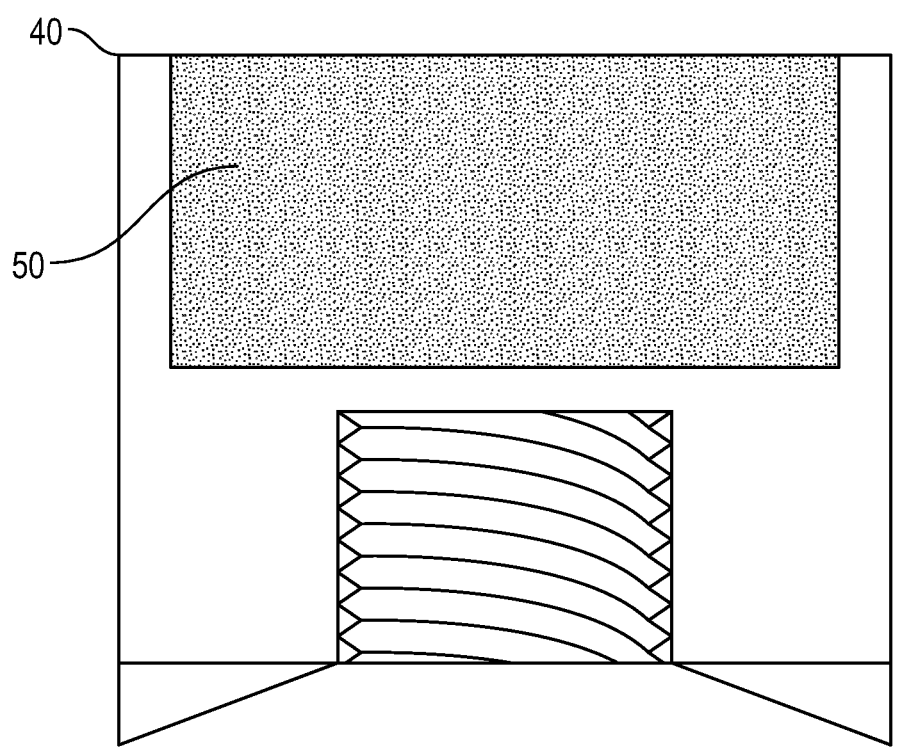
FIG. 43 illustrates a cross-sectional side view of a flush syringe with a seal and a cap in accordance with one or more embodiments of the present disclosure.

In an alternate embodiment, as shown in FIG. 43, the syringe assembly has a disinfectant cap 40 attached to the front of the syringe, which creates a visual reminder to clinician to disinfect the surface before using the syringe content, but it will not combine the two steps into one. As shown in FIG. 43, a clinician will remove the tip cap or peel, disinfect the hub with the syringe and cap attached by scrubbing the surface, then detaches the cap which then exposes the syringe tip, then connects the syringe to the connector and continues as normal. The cap can be snapped onto the barrel or can get threaded onto the outside surface of the collar around the luer tip as seen in the image named 'detachable cap'. Other embodiment is one where the swab is not porous and only the surfaces that come into contact with the needleless connector are coated with an antimicrobial coating. As shown in FIG. 43, cap 40 encloses disinfectant-loaded swab 50 and cap 40 includes threads to be threaded onto a corresponding luer component that has threads on the internal and/or external surfaces.

A seal may be placed on the open end to contain the disinfectant or antimicrobial agent within the chamber until the seal is removed and the syringe assembly 10 is connected to a vascular access device 60. The absorbent material of disinfectant-loaded swab 50 will soak up the disinfectant or antimicrobial agent and will disinfect the hub of a vascular access device upon connection.

The syringe assembly 10 may be filled with flush solution using known methods. Additionally, the syringe assembly 10 may be provided pre-filled from the manufacturer or supplier. The flush solution may be any solution intended for flushing or maintaining performance of VAD's. It is preferred that the flush solution be selected from the group consisting of saline flush solution and heparin lock flush solution. These solutions are known in the art and are readily available. An example of a saline flush solution includes, but is not limited to, 0.9% sodium chloride USP for injection. An example of a heparin lock flush solution includes but is not limited to 0.9% sodium chloride with 100 USP units of heparin sodium per mL or 10 USP units of heparin sodium per mL.

Once the connection of the syringe assembly 10 to the VAD is completed, fluid communication from the barrel 20 of the syringe to the vascular access device can occur. Fluid is drawn from the barrel 20 through the integral passageway 27 into the IV or catheter. Because of the presence of the disinfectant-loaded swab 50 in the collar 30, fluid communication through a vascular access device and into a patient is conducted under aseptic conditions without any additional swabbing steps and diligence on the part of the clinician.

In one or more embodiments, the collar 30 is integrally formed on the distal wall 25 of the syringe barrel 20 for fluid communication to the vascular access device.

The barrel 20 may also include an elongate tip 26 which extends distally from the barrel. The tip 26 can have an outer diameter that is different from or the same as the outer diameter of the rest of the barrel. The tip of the barrel may include a luer slip connection or a locking luer type collar concentrically surrounding the tip or within the tip.

As shown in FIG. 1, an elongated plunger rod 100 may include a distal portion and a proximal portion, the plunger rod further comprising a distal end including a stopper slidably positioned in fluid-tight engagement with the inside surface of the barrel for drawing fluid into and driving fluid out of the chamber by movement of the stopper relative to the barrel, the elongated plunger rod extending outwardly from the open proximal end 23 of the barrel, the stopper having a distal surface.

An elongate plunger rod 100 may be disposed within the barrel 20. The plunger rod includes an elongate body portion with a proximal end and a distal end.

The elongate body portion of the plunger rod has an axial length extending from the proximal end to the distal end. The body portion may include a single beam or features, which may have cylindrical or other shapes. The body portion may be formed by two perpendicularly intersecting beams.

The plunger rod may also include a thumbpress at the proximal end of the elongate body portion. The shape of the thumbpress can vary depending on the desired usage of the flush syringe assembly. The shape of the thumbpress may be round, square, rectangular, triangular, oval, pentagonal, hexagonal and cruciform.

A stopper can be connected to the distal end of the plunger rod. The shape and size of the stopper can be any suitable shape or size depending on, for example, the shape and size of the barrel and plunger rod. The plunger rod is slidably positioned in the barrel so that the stopper is in fluid-tight contact with the inside surface of the barrel and so that distal movement of the plunger rod relative to the barrel causes the stopper to push the fluid out of the barrel. In some embodiments, the stopper is slidably positioned in fluid-tight contact with the inside surface of the barrel for driving fluid out of the chamber by movement of the stopper relative to the barrel. The stopper can be connected to the distal end of the elongate plunger rod by any suitable means. In some embodiments, the stopper is connected by a mechanical connection such as interaction of complementary screw threads and press-fit connections. The stopper may be slidably positioned in fluid-tight engagement with the inside surface of the barrel for drawing fluid into and driving fluid out of the chamber.

The stopper may be made of any material suitable for providing a seal with the inside surface of the barrel. For example, the stopper may be made of thermoplastic elastomers, natural rubber, synthetic rubber or thermoplastic materials and combinations thereof. The stopper may be integrally formed or composed of separate components of the same or different materials joined together. The plunger rod may be made of material which is more rigid than the stopper such as polypropylene, polyethylene and the like. Materials should be chosen to be compatible with the procedure being used.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as disclosed.

What is claimed is:

1. A flush syringe assembly comprising:
    a barrel including a side wall having an inside surface defining a chamber for retaining a fluid, an open proximal end, a distal end including a distal wall with an elongate tip and an outer rim extending distally therefrom, the elongate tip having a passageway therethrough in fluid communication with said chamber, the outer rim having a plurality of threads on an inside surface of the outer rim for connection to a vascular access device;
    a collar extending from the distal wall of the barrel, the collar including at least one side wall having an inside surface defining a compartment, an open distal end, a proximal end adjacent the distal wall of the barrel;
    a disinfectant-loaded swab disposed in the collar; and
    an elongated plunger rod disposed within the barrel, the elongated plunger rod comprising a distal end and a proximal end, the distal end of the elongated plunger rod including a stopper slidably positioned in fluid-tight engagement with the inside surface of the barrel for drawing fluid into and driving fluid out of the chamber by movement of the stopper relative to the barrel, the elongated plunger rod extending outwardly from the open proximal end of the barrel, the stopper having a distal surface;
    wherein the collar surrounds the swab, the outer rim, and the elongate tip, the swab surrounds the outer rim and the elongate tip, and the outer rim surrounds the elongate tip.

2. The flush syringe assembly of claim 1, wherein the fluid is a flush fluid.

3. The flush syringe assembly of claim 1, wherein the disinfectant-loaded swab has one or more openings or slits on a top surface of the disinfectant-loaded swab.

4. The flush syringe assembly of claim 1, wherein the compartment of the collar surrounds the elongate tip.

5. The flush syringe assembly of claim 1, wherein the disinfectant-loaded swab is made of an absorbent material.

6. The flush syringe assembly of claim 1, wherein the disinfectant-loaded swab includes a disinfectant or antimicrobial agent selected from the group consisting of ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

7. A flush syringe assembly comprising:
    a barrel including a side wall having an inside surface defining a chamber for retaining a fluid, an open proximal end, a distal end including a distal wall with an elongate tip and an outer rim extending distally therefrom, the elongate tip having a passageway therethrough in fluid communication with said chamber, the outer rim having a plurality of threads on an inside surface of the outer rim for connection to a vascular access device;
    a collar extending from the distal wall of the barrel, the collar including at least one side wall having an inside surface defining a compartment, an open distal end, a proximal end adjacent the distal wall of the barrel;
    a disinfectant-loaded swab disposed in the collar;
    a removable cap having a body, a proximal end, and a closed distal end, the removable cap being mounted on the open distal end of the collar;
    an elongated plunger rod disposed within the barrel, the elongated plunger rod comprising a distal end and a proximal end; and
    a stopper slidably disposed on the distal end of the plunger rod and positioned in fluid-tight engagement with the inside surface of the barrel for drawing fluid into and driving fluid out of the chamber by movement of the stopper relative to the barrel;
    wherein the collar surrounds the swab, the outer rim, and the elongate tip, the swab surrounds the outer rim and the elongate tip, and the outer rim surrounds the elongate tip;
    wherein an outside surface of a distal wall of the collar includes a plurality of threads to connect the collar to the removable cap.

8. The flush syringe assembly of claim 7, wherein the compartment of the collar surrounds the elongate tip.

9. The flush syringe assembly of claim 7, wherein the fluid is a flush fluid.

10. The flush syringe assembly of claim 7, wherein the removable cap includes an outward protrusion extending from the body of the removable cap and corresponding with the passageway on a distal end of the elongate tip.

11. The flush syringe assembly of claim 7, wherein the removable cap has a cross-sectional shape that is triangular, square, pentagonal, hexagonal, heptagonal, octagonal, symmetric or non-symmetric polygonal.

12. The flush syringe assembly of claim 7, wherein the collar has a cross-sectional shape that is triangular, square, pentagonal, hexagonal, heptagonal, octagonal, symmetric or non-symmetric polygonal.

13. The flush syringe assembly of claim 7, wherein the disinfectant-loaded swab is made of an absorbent material.

14. The flush syringe assembly of claim 7, wherein the disinfectant-loaded swab includes a disinfectant or antimicrobial agent selected from the group consisting of ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

* * * * *